(12) United States Patent
Zhang et al.

(10) Patent No.: US 11,665,959 B2
(45) Date of Patent: May 30, 2023

(54) COMPOUND, ORGANIC ELECTROLUMINESCENT DEVICE AND DISPLAY EQUIPMENT

(71) Applicants: WUHAN TIANMA MICROELECTRONICS CO., LTD., Wuhan (CN); WUHAN TIANMA MICROELECTRONICS CO., LTD. SHANGHAI BRANCH, Shanghai (CN)

(72) Inventors: Lei Zhang, Shanghai (CN); Wei Gao, Shanghai (CN); Wenpeng Dai, Shanghai (CN); Jinghua Niu, Shanghai (CN)

(73) Assignees: WUHAN TIANMA MICROELECTRONICS CO., LTD., Wuhan (CN); WUHAN TIANMA MICROELECTRONICS CO., LTD. SHANGHAI BRANCH, Shanghai (CN)

(*) Notice: Subject to any disclaimer, the term of this patent is extended or adjusted under 35 U.S.C. 154(b) by 388 days.

(21) Appl. No.: 16/731,079

(22) Filed: Dec. 31, 2019

(65) Prior Publication Data

US 2021/0098710 A1    Apr. 1, 2021

(30) Foreign Application Priority Data

Sep. 29, 2019    (CN) .......................... 201910936389.3

(51) Int. Cl.
*C07D 403/14* (2006.01)
*H01L 51/00* (2006.01)
(Continued)

(52) U.S. Cl.
CPC ........ *H01L 51/0071* (2013.01); *C07D 403/14* (2013.01); *C07D 405/14* (2013.01);
(Continued)

(58) Field of Classification Search
None
See application file for complete search history.

(56) References Cited

U.S. PATENT DOCUMENTS

| | | | |
|---|---|---|---|
| 2007/0057250 A1* | 3/2007 | Takiguchi | .............. C09K 11/06 257/40 |
| 2014/0163237 A1* | 6/2014 | Sisk | ...................... C07D 413/14 548/219 |

(Continued)

FOREIGN PATENT DOCUMENTS

| | | | | |
|---|---|---|---|---|
| CN | 104650042 A | * | 5/2015 | ........... C07D 403/14 |
| CN | 106753340 A | * | 5/2017 | ............. C09K 11/06 |

(Continued)

OTHER PUBLICATIONS

Ban, Xinxin, et al. "Systematically tuning the Δ E ST and charge balance property of bipolar hosts for low operating voltage and high power efficiency solution-processed electrophosphorescent devices." Journal of Materials Chemistry C 3.19 (2015): 5004-5016. (Year: 2015).*

(Continued)

*Primary Examiner* — Robert S Loewe
(74) *Attorney, Agent, or Firm* — Kilpatrick Townsend & Stockton LLP

(57) ABSTRACT

The present disclosure relates to the field of organic electroluminescence technology, and in particular to a compound, an organic electroluminescent device, and a display (Continued)

equipment. The compound of the present disclosure has the structure shown in Formula (I).

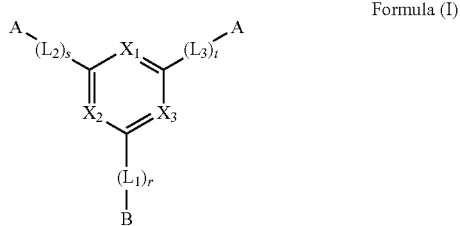

Formula (I)

15 Claims, 1 Drawing Sheet

(51) Int. Cl.
C07D 405/14 (2006.01)
H01L 51/50 (2006.01)

(52) U.S. Cl.
CPC ...... H01L 51/0067 (2013.01); H01L 51/0073 (2013.01); H01L 51/5096 (2013.01)

(56) References Cited

U.S. PATENT DOCUMENTS

| | | | |
|---|---|---|---|
| 2014/0284581 A1* | 9/2014 | Zheng | H01L 51/0061 548/219 |
| 2014/0284584 A1* | 9/2014 | Zheng | C07D 403/14 257/40 |
| 2018/0248128 A1* | 8/2018 | Huang | C07D 403/14 |
| 2019/0027695 A1* | 1/2019 | Zhang | C07D 401/14 |
| 2019/0071430 A1* | 3/2019 | Zhang | C07D 405/14 |
| 2020/0052229 A1* | 2/2020 | Yam | C07D 271/107 |

FOREIGN PATENT DOCUMENTS

| | | | | |
|---|---|---|---|---|
| CN | 108503636 A | | 9/2018 | |
| JP | 2009158848 A | * | 7/2009 | H01L 51/50 |
| WO | WO-2018192227 | * | 10/2018 | C07D 403/14 |

OTHER PUBLICATIONS

Ban, Xinxin, et al. "Bipolar host with multielectron transport benzimidazole units for low operating voltage and high power efficiency solution-processed phosphorescent OLEDs." ACS Applied Materials & Interfaces 7.13 (2015): 7303-7314. (Year: 2015).*

Jiang, Wei, et al. "Ideal bipolar host materials with bis-benzimidazole unit for highly efficient solution-processed green electrophosphorescent devices." Organic letters 16.20 (2014): 5346-5349. (Year: 2014).*

* cited by examiner

COMPOUND, ORGANIC ELECTROLUMINESCENT DEVICE AND DISPLAY EQUIPMENT

CROSS-REFERENCE TO RELATED APPLICATION

This application claims priority of Chinese Patent Application No. 201910936389.3, filed on Sep. 29, 2019, which is hereby incorporated by reference in its entirety.

FIELD

The present disclosure relates to the field of organic electroluminescence technology, and in particular to a compound, an organic electroluminescent device, and display equipment.

BACKGROUND

Currently widely used electron transport materials, such as batho-phenanthroline (BPhen), bathocuproine (BCP) and TmPyPB, generally meet the market demand for organic electroluminescent panels, but their glass transition temperature is low, generally less than 85° C. When the device is in operation, the Joule heat generated will lead to molecular degradation and molecular structure changes, resulting in lower panel efficiency and poorer thermal stability. At the same time, this molecular structure symmetrization is very regular, and it is easy to crystallize after a long time. Once the electron transport material crystallizes, the intermolecular charge transition mechanism will be different from the normally operated amorphous film mechanism, resulting in a decrease in the performance of electron transporting, and the electron mobility and hole mobility of the entire device are unbalanced, and the exciton formation efficiency is greatly reduced, and the exciton formation will be concentrated at the interface between the electron transport layer and the light emitting layer, resulting in a serious decrease in the efficiency and service life of the device.

SUMMARY

The present disclosure provides a compound, an organic electroluminescent device including the same, and a display equipment having the organic electroluminescent device.

According to an embodiment of the present disclosure, there is provided a compound having the structure shown in Formula (I),

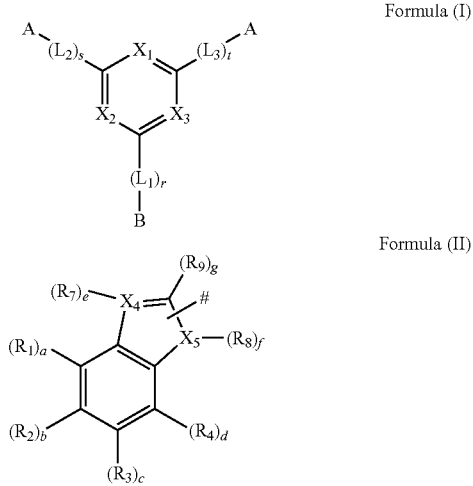

Formula (I)

Formula (II)

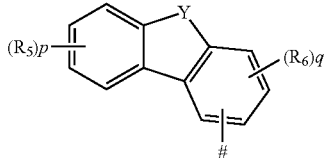

Formula (III)

In one embodiment, $X_1$-$X_3$ are each independently selected from an N atom, or a C atom; and $L_1$-$L_3$ are each independently selected from substituted or unsubstituted $C_5$-$C_{40}$ aryl, substituted or unsubstituted $C_3$-$C_{40}$ heteroaryl; and r, s, and t are each independently selected from 0, or 1;

A is the structure shown in Formula (II), and B is the structure shown in Formula (III);

in Formula (II), $X_4$ and $X_5$ are each independently selected from a C atom, or an N atom, and at least one of them is a N atom; and a to g are each independently selected from 0, or 1;

in Formula (III), Y is selected from an N atom, an O atom, or an S atom; and p and q are each independently selected from 1, 2, or 3;

$R_1$-$R_9$ are each independently selected from $C_1$-$C_{12}$ alkyl, substituted or unsubstituted $C_5$-$C_{40}$ aryl, and substituted or unsubstituted $C_3$-$C_{40}$ heteroaryl;

represents the connection location.

According to one embodiment of the present disclosure, $X_1$-$X_3$ are all C atoms.

According to one embodiment of the present disclosure, $R_1$-$R_9$ are each independently selected from substituted or unsubstituted phenyl.

According to one embodiment of the present disclosure, A is a structure shown in Formula (II-1) or Formula (II-2),

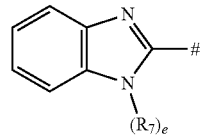

Formula (II-1)

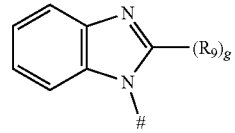

Formula (II-2)

In one embodiment, $R_7$ and $R_9$ are each independently selected from $C_1$-$C_{12}$ alkyl, substituted or unsubstituted $C_5$-$C_{40}$ aryl, and substituted or unsubstituted $C_3$-$C_{40}$ heteroaryl; and e and g are each independently selected from 0, or 1;

represents the connection location.

According to one embodiment of the present disclosure, $R_7$ and $R_9$ are each independently selected from substituted or unsubstituted phenyl.

According to one embodiment of the present disclosure, $L_2$ is identical to $L_3$, and s is identical to t.

According to one embodiment of the present disclosure, r, s, and t are all 0.

According to one embodiment of the present disclosure, one of a to f is 1, and others are 0.

According to one embodiment of the present disclosure, g is 1.

According to one embodiment of the present disclosure, one of p and q is 1, and the other is 0.

According to one embodiment of the present disclosure, $L_1$-$L_3$ are each independently selected from one or more of the following groups:

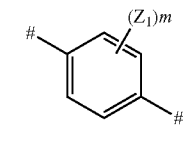
Chemical Formula 2-1

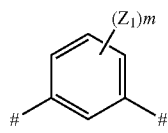
Chemical Formula 2-2

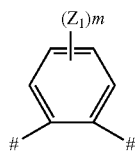
Chemical Formula 2-3

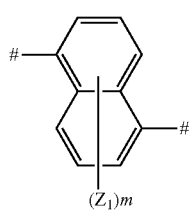
Chemical Formula 2-4

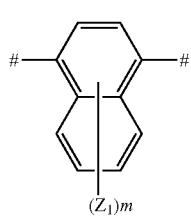
Chemical Formula 2-5

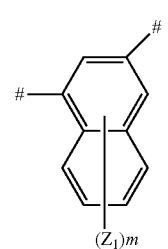
Chemical Formula 2-6

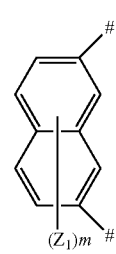
Chemical Formula 2-7

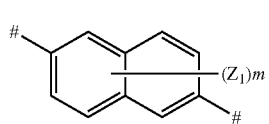
Chemical Formula 2-8

-continued

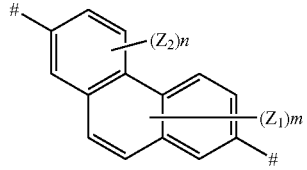
Chemical Formula 2-9

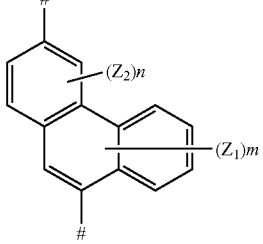
Chemical Formula 2-10

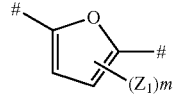
Chemical Formula 2-11

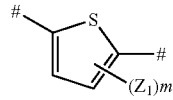
Chemical Formula 2-12

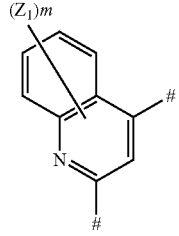
Chemical Formula 2-13

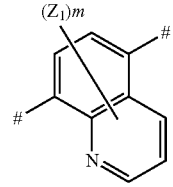
Chemical Formula 2-14

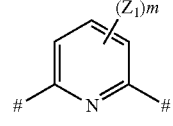
Chemical Formula 2-15

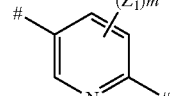
Chemical Formula 2-16

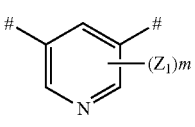
Chemical Formula 2-17

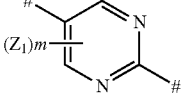
Chemical Formula 2-18

Chemical Formula 2-19

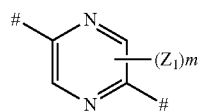

Chemical Formula 2-20

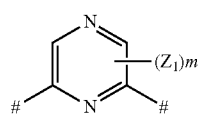

Chemical Formula 3-1

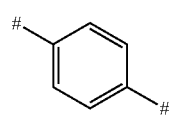

Chemical Formula 3-2

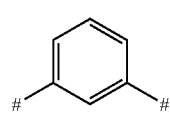

Chemical Formula 3-3

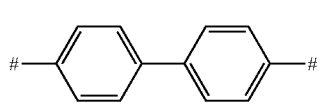

Chemical Formula 3-4

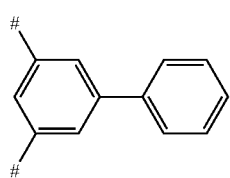

Chemical Formula 3-5

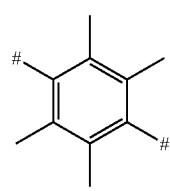

Chemical Formula 3-6

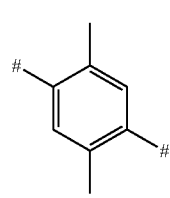

Chemical Formula 3-7

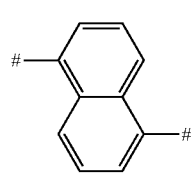

Chemical Formula 3-8

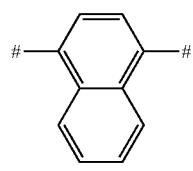

Chemical Formula 3-9

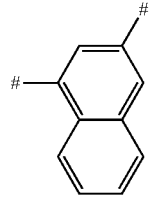

Chemical Formula 3-10

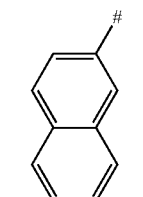

Chemical Formula 3-11

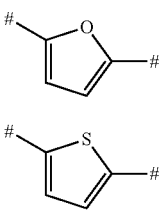

Chemical Formula 3-12

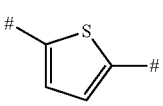

Chemial Formula 3-13

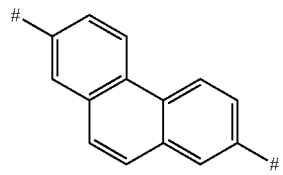

Chemical Formula 3-14

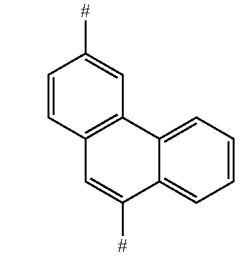

Chemical Formula 3-15

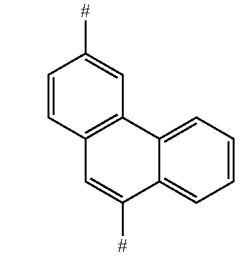

Chemical Formula 3-16

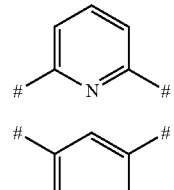

In one embodiment, $Z_1$ and $Z_2$ are each independently selected from any one or more of $C_1$-$C_{10}$ alkyl, $C_3$-$C_{10}$ cycloalkyl, $C_2$-$C_{10}$ alkenyl, $C_1$-$C_6$ alkoxyl, halogen, cyano, $C_6$-$C_{30}$ monocyclic aromatic hydrocarbon or fused ring aromatic hydrocarbon group, and $C_3$-$C_{30}$ monocyclic heteroaromatic hydrocarbon or fused ring heteroaromatic hydrocarbon group; m and n are each independently selected from 0, 1, or 2; and #represents the connection location.

According to one embodiment of the present disclosure, $Z_1$ and $Z_2$ are each independently selected from $C_6$-$C_{30}$ monocyclic heteroaromatic hydrocarbon or fused ring heteroaromatic hydrocarbon group.

According to one embodiment of the present disclosure, the compound has the structure shown in Formula (I-1),

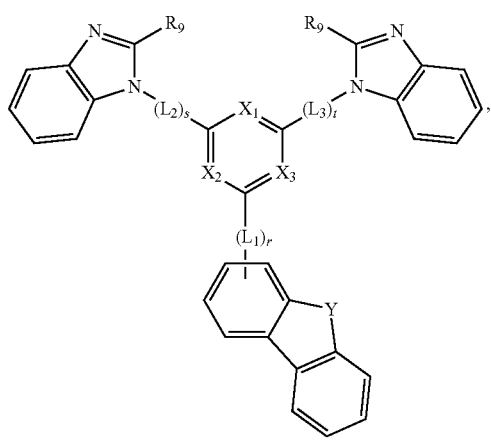

Formula (I-1)

In one embodiment, $X_1$-$X_3$ are each independently selected from an N atom, or a C atom; and $L_1$-$L_3$ are each independently selected from substituted or unsubstituted $C_5$-$C_{40}$ aryl, substituted or unsubstituted $C_3$-$C_{40}$ heteroaryl; r, s, and t are each independently selected from 0, or 1; and Y is selected from an N atom, an O atom, or an S atom.

According to one embodiment of the present disclosure, r, s, and t are all 0.

According to one embodiment of the present disclosure, $R_1$-$R_9$ are each independently selected from substituted or unsubstituted $C_5$-$C_{40}$ aryl, substituted or unsubstituted $C_3$-$C_{40}$ heteroaryl; and the substituent is selected from any one or more of $C_1$-$C_{10}$ alkyl, $C_3$-$C_{10}$ cycloalkyl, $C_2$-$C_{10}$ alkenyl, $C_1$-$C_6$ alkoxyl, halogen, cyano, $C_6$-$C_{30}$ monocyclic aromatic hydrocarbon or fused ring aromatic hydrocarbon group, and $C_3$-$C_{30}$ monocyclic heteroaromatic hydrocarbon or fused ring heteroaromatic hydrocarbon group.

According to one embodiment of the present disclosure, the compound is selected from any one of

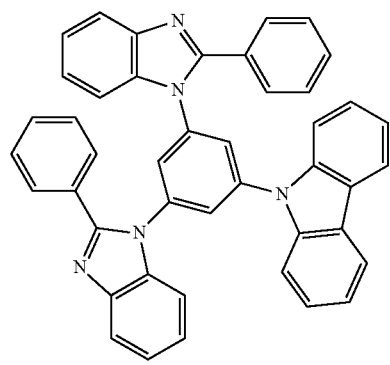

HB01

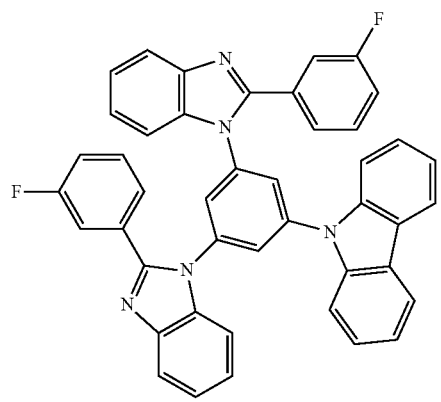

HB02

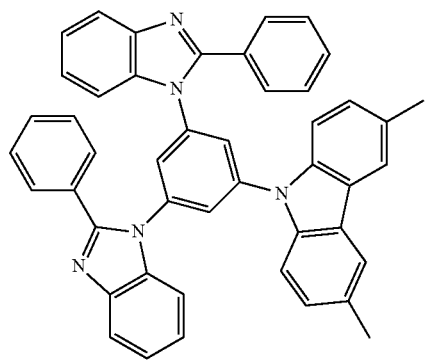

HB03

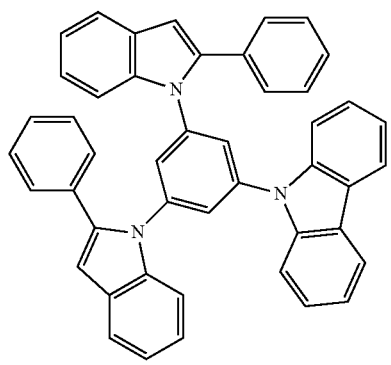

HB04

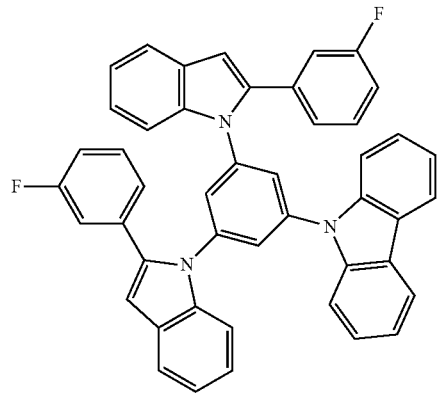

HB05

HB06 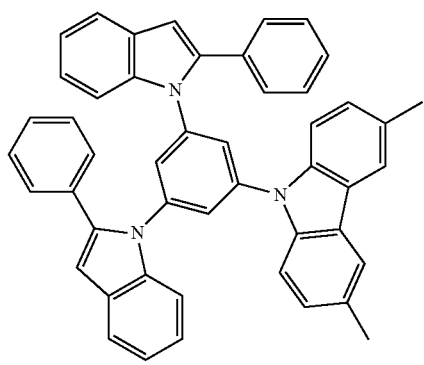
HB10 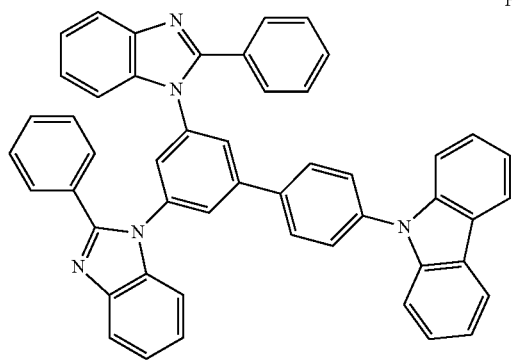
HB07 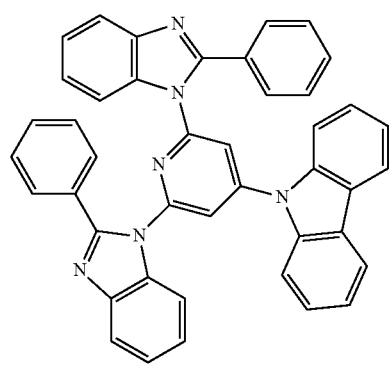
HB11 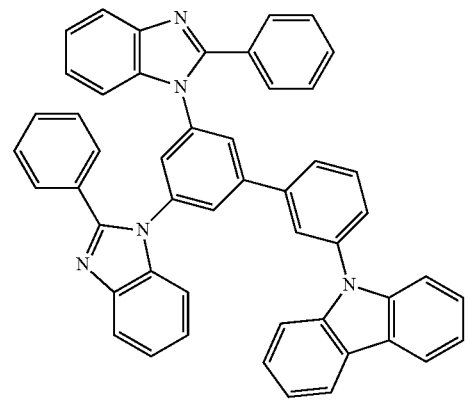
HB08 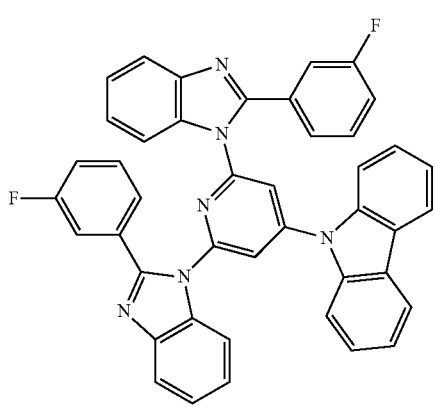
HB12 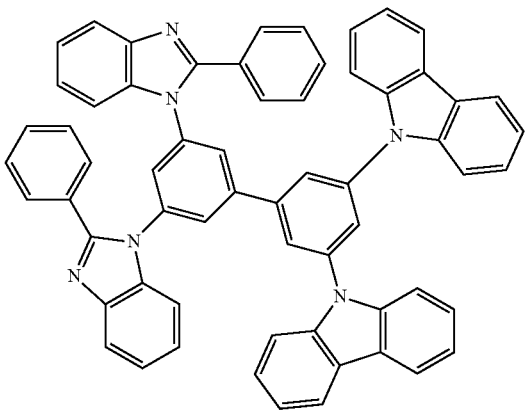
HB09 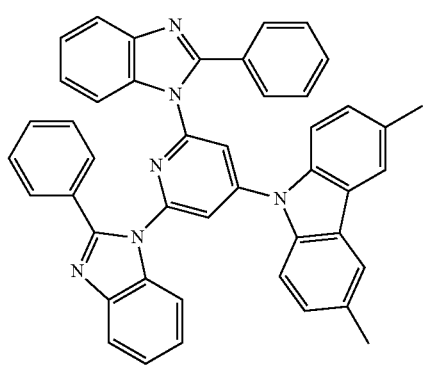
HB13 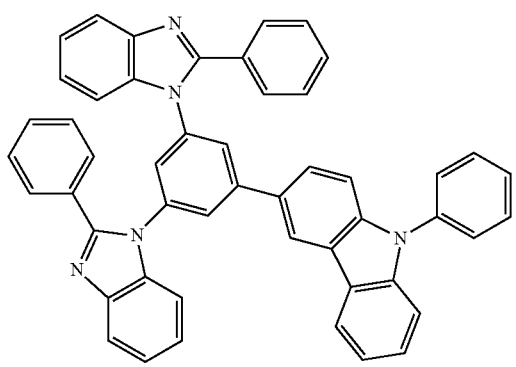

HB14 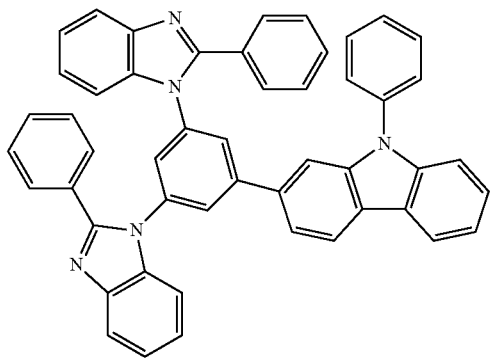
HB15 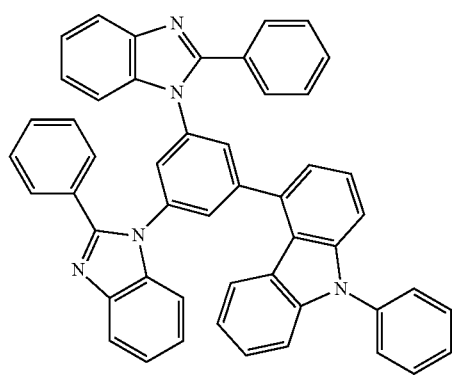
HB16 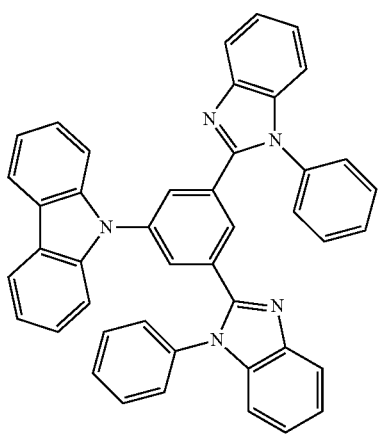
HB17 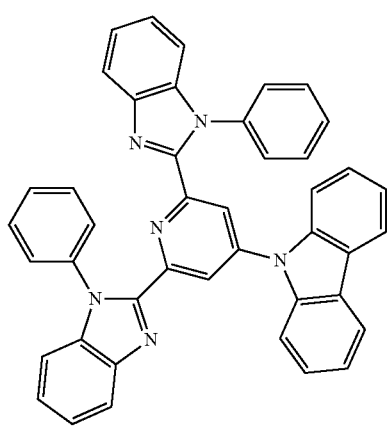
HB18 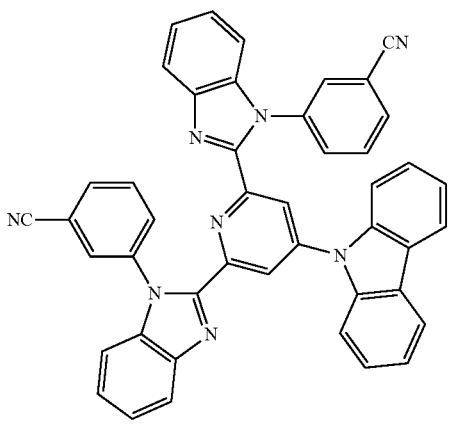
HB19 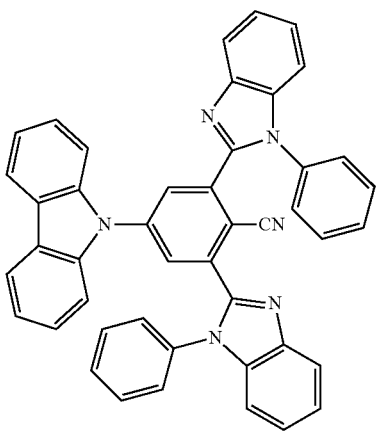
HB20 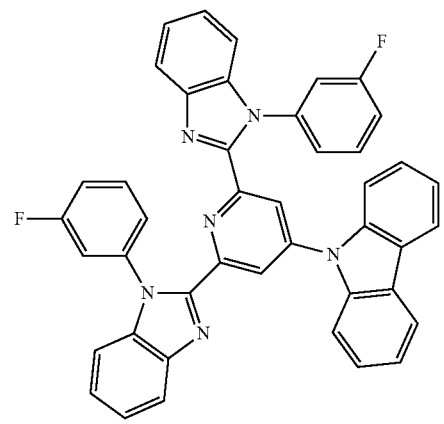

HB21
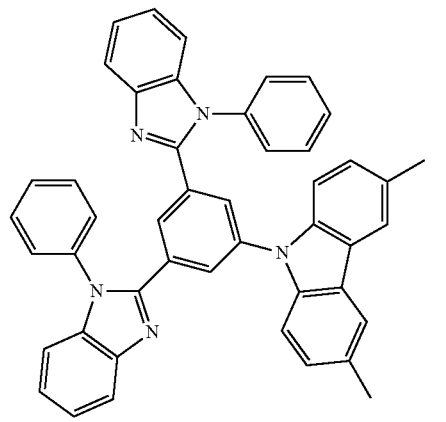
HB22
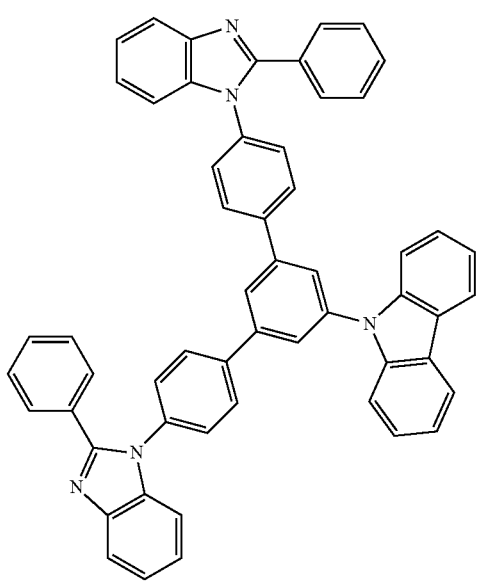
HB23
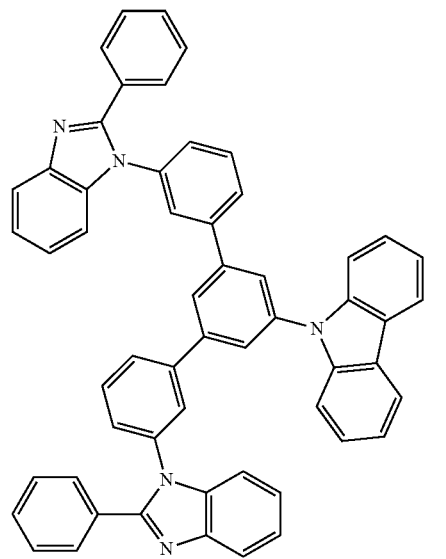
HB24
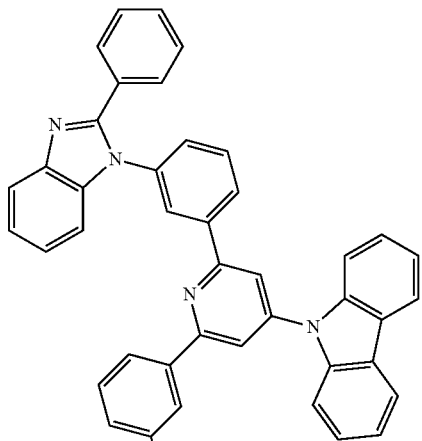
HB25
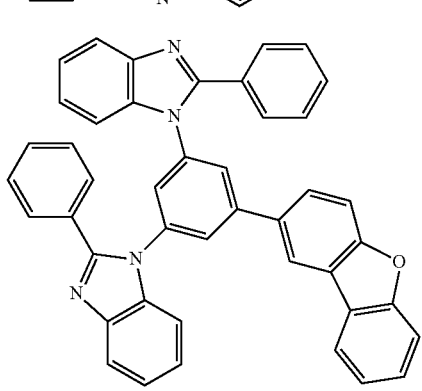
HB26
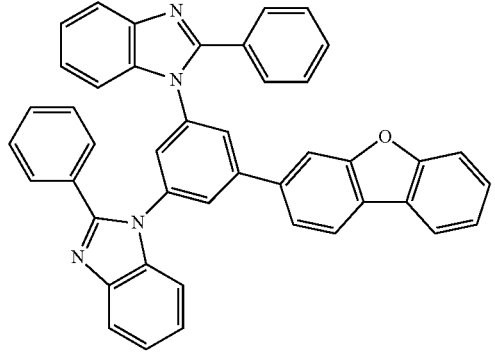
HB27
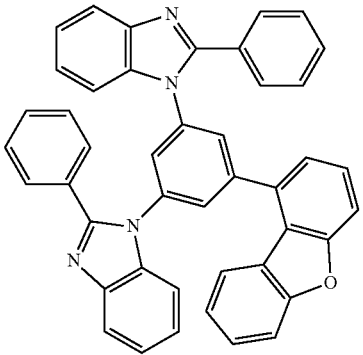

-continued
HB28
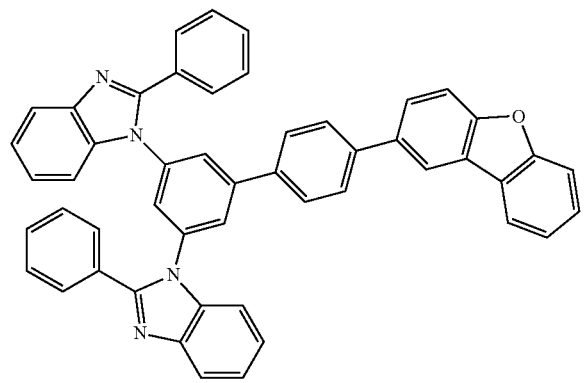
HB29
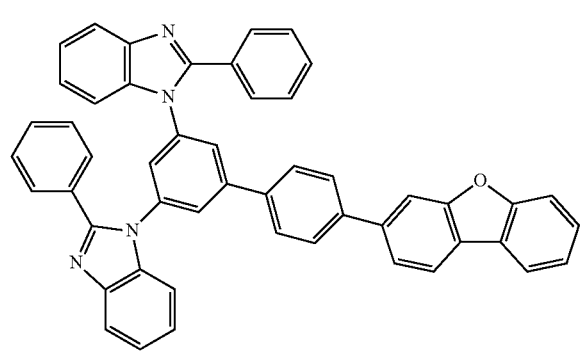
HB30
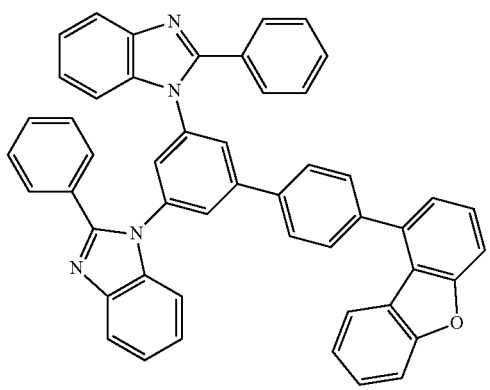
HB31
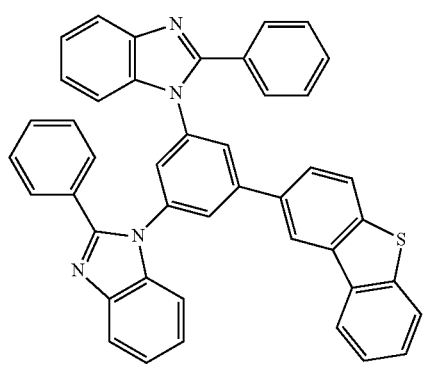
HB32
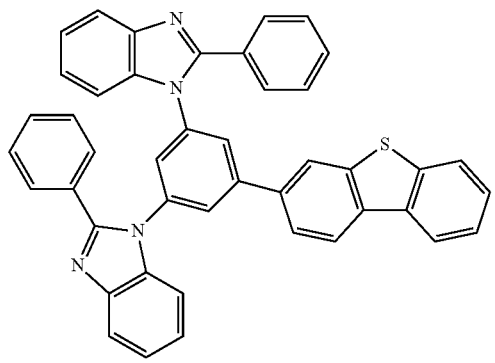
HB33
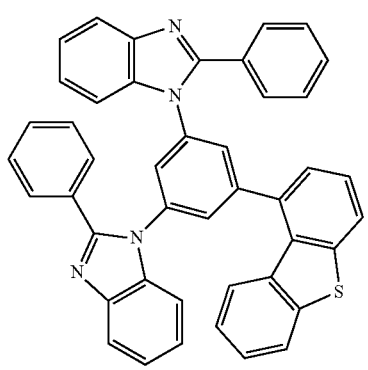
HB34
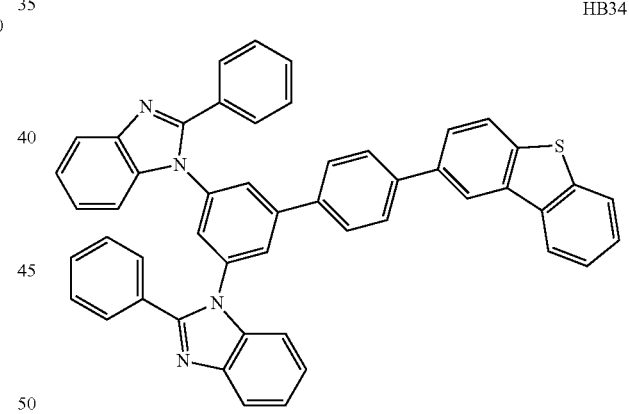
HB35
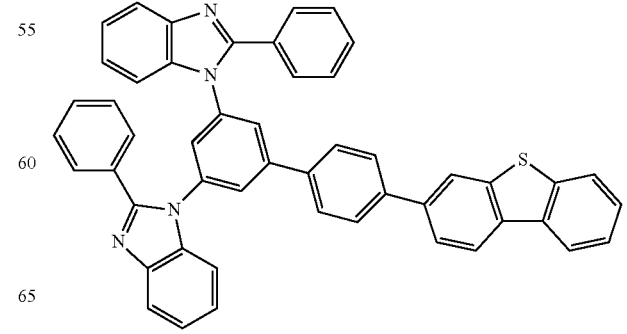

HB36
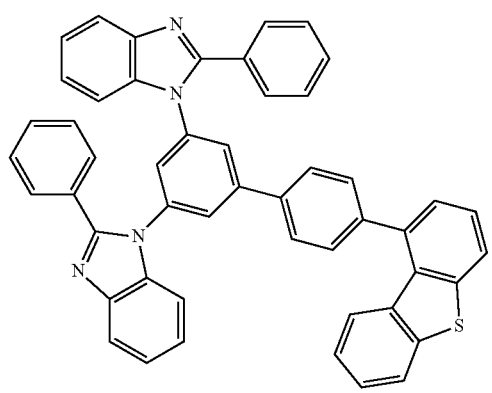
HB37
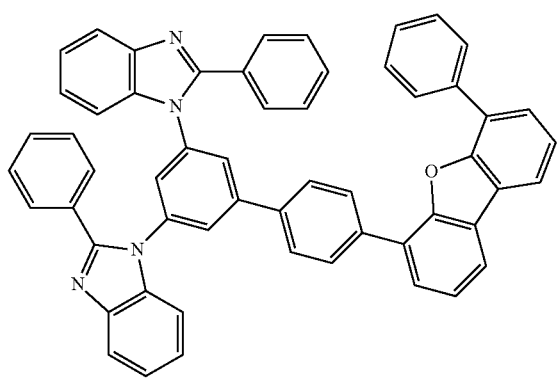
HB38
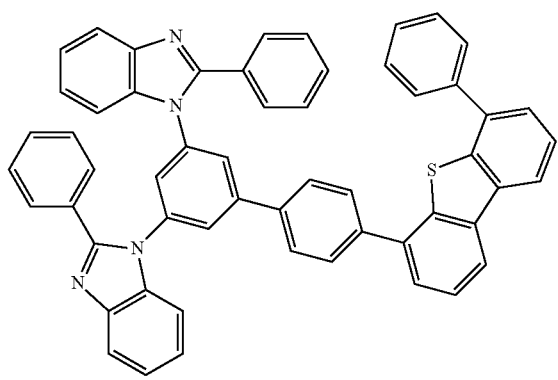
HB39
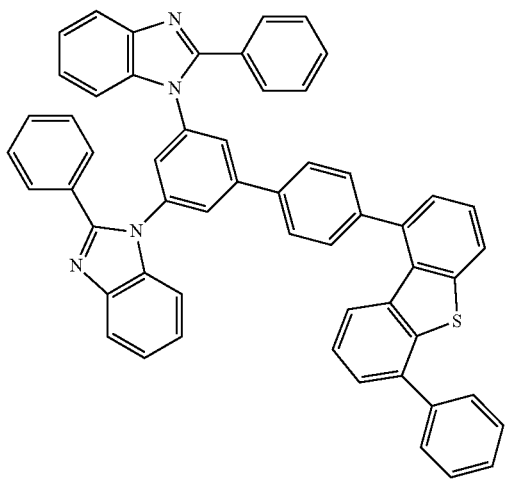
HB40
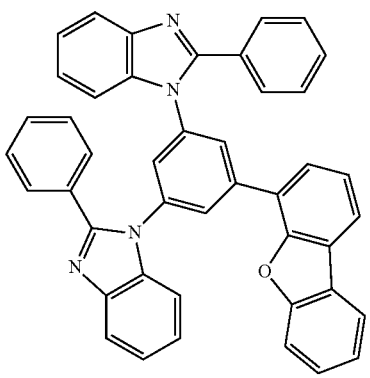
HB41
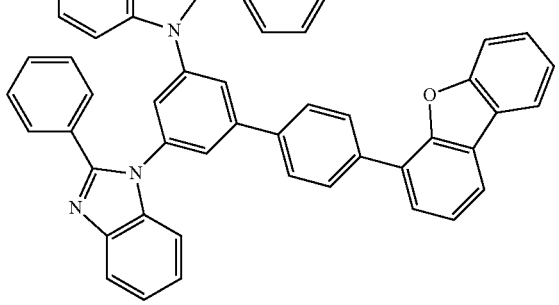
HB42
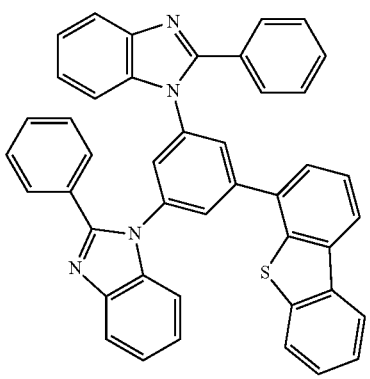

HB43
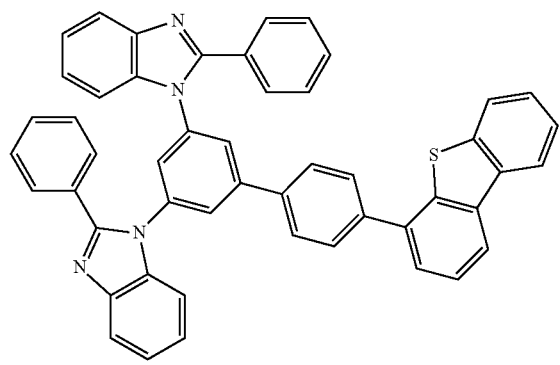
HB44
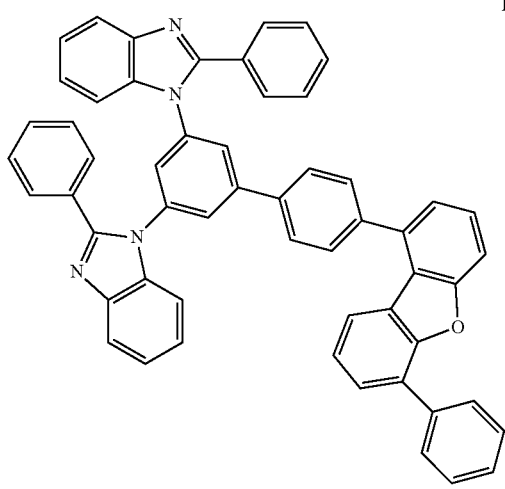
HB45
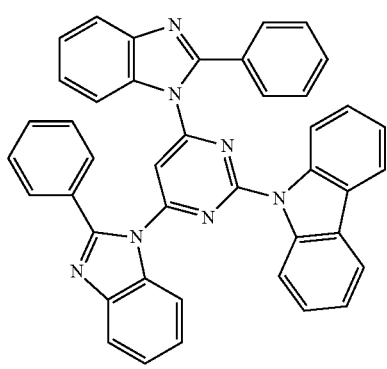
HB46
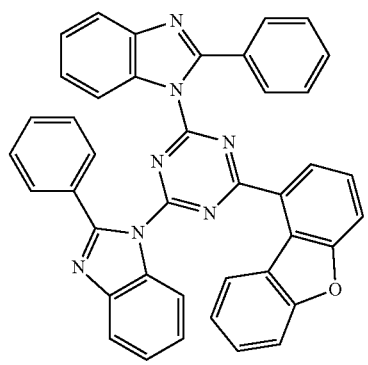
HB47
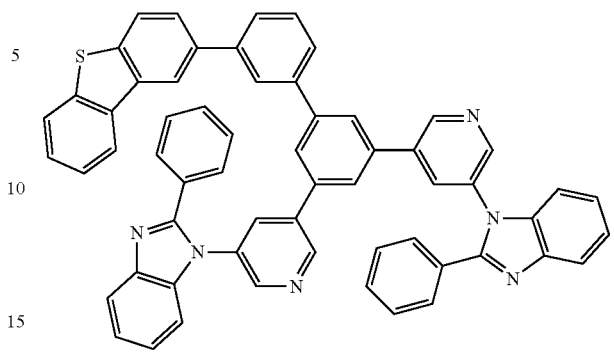
HB48
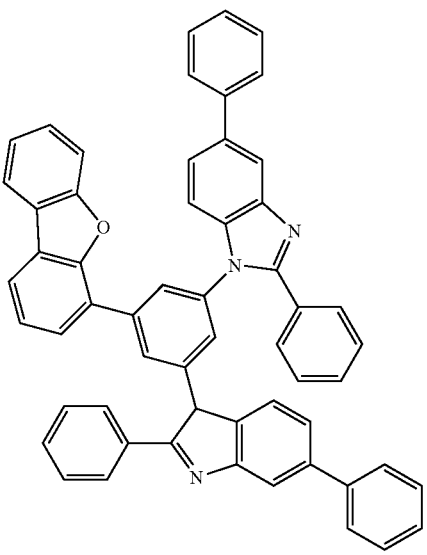
HB49
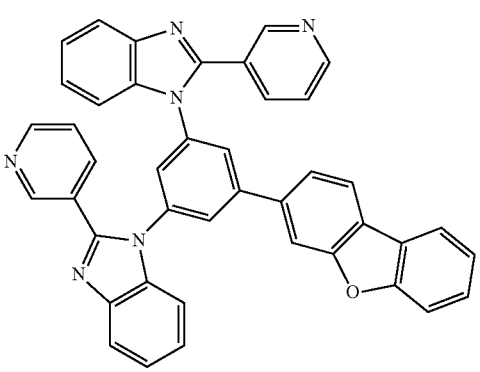
HB50
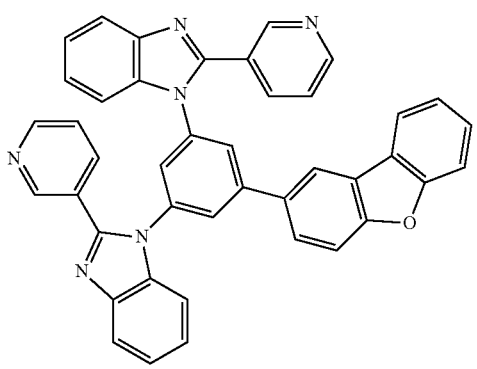

HB51

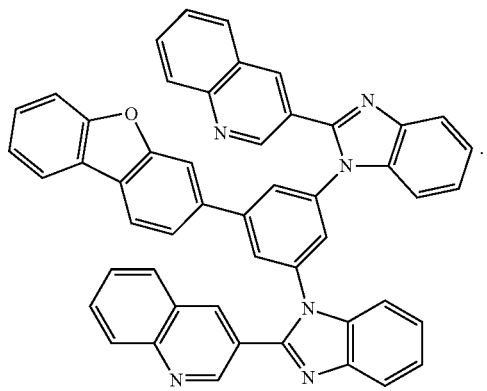

HB01

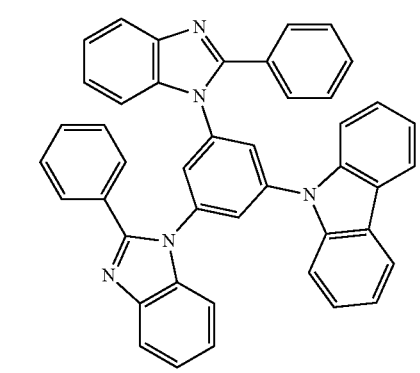

HB18

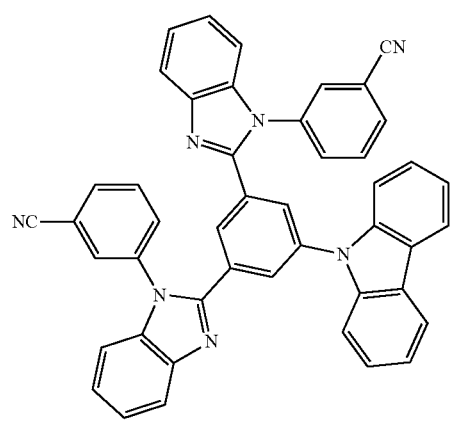

According to one embodiment of the present disclosure, the compound is selected from any one of

HB25

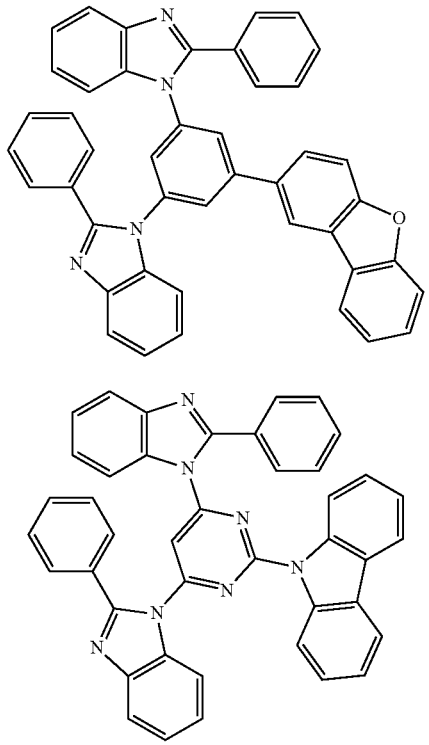

HB45

HB48

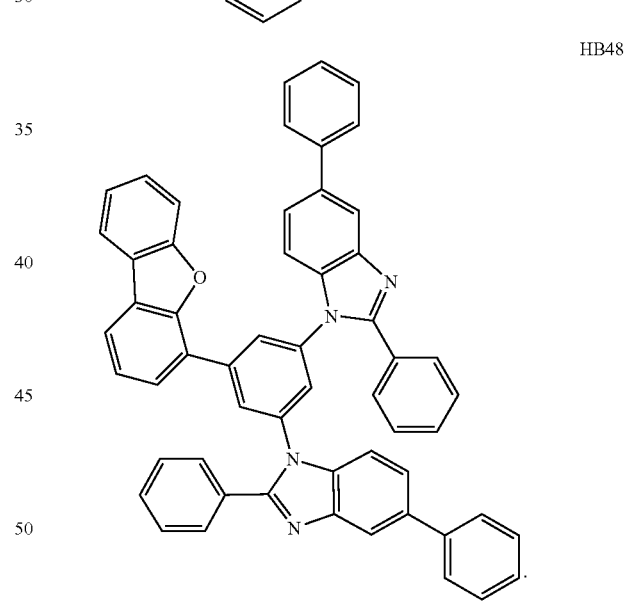

According to another embodiment of the present disclosure, there is provided an organic electroluminescent device including a first electrode and a second electrode, and an organic functional layer located between the first electrode and the second electrode, and the organic functional layer includes a hole-blocking layer, and the transport material of the hole-blocking layer includes the compound according to the present disclosure.

According to another embodiment of the present disclosure, there is provided a display equipment including the organic electroluminescent device according to the present disclosure.

DETAILED DESCRIPTION OF THE EMBODIMENTS

Figure 1:
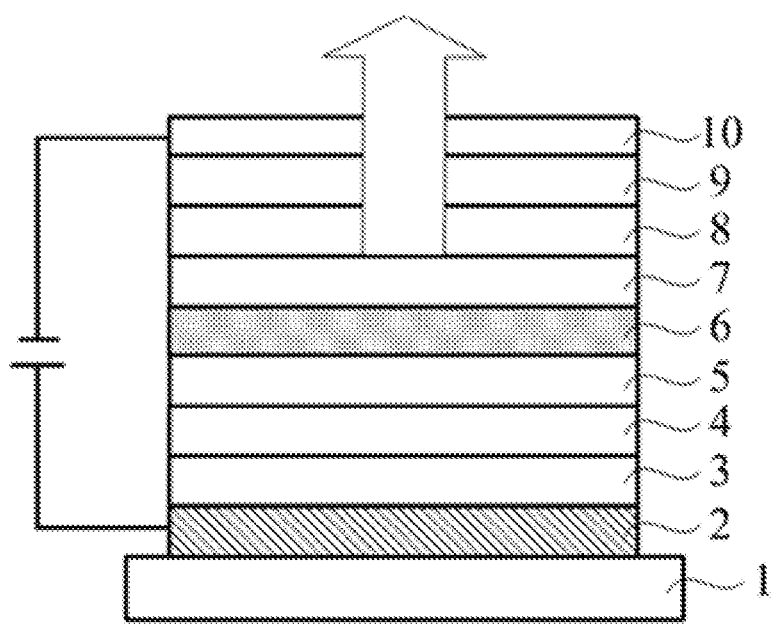
FIG. 1 is a structural schematic diagram of the organic electroluminescent device according to the present disclosure.

The particular embodiments are only demonstration of the present disclosure and do not constitute a restriction to the content of the present disclosure. The following will further explain and describe the present disclosure in combination with the particular embodiments.

The present disclosure provides a compound, an organic electroluminescent device including the same, and a display equipment having the organic electroluminescent device.

According to an embodiment of the present disclosure, there is provided a compound having the structure shown in Formula (I),

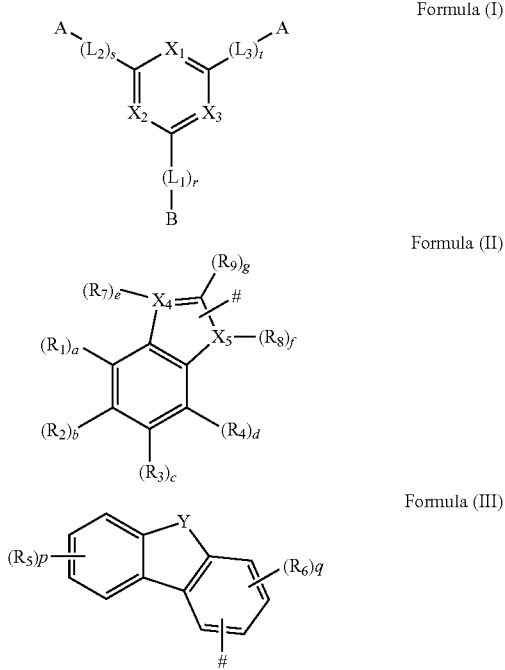

In one embodiment, $X_1$-$X_3$ are each independently selected from an N atom, or a C atom; and $L_1$-$L_3$ are each independently selected from substituted or unsubstituted $C_5$-$C_{40}$ aryl, substituted or unsubstituted $C_3$-$C_{40}$ heteroaryl; and r, s, and t are each independently selected from 0, or 1;

A is the structure shown in Formula (II), and B is the structure shown in Formula (III); in Formula (II), $X_4$ and $X_5$ are each independently selected from a C atom, or an N atom, and at least one of them is an N atom; and a to g are each independently selected from 0, or 1;

in Formula (III), Y is selected from an N atom, an O atom, or an S atom; and p and q are each independently selected from 1, 2, or 3;

$R_1$-$R_9$ are each independently selected from $C_1$-$C_{12}$ alkyl, substituted or unsubstituted $C_5$-$C_{40}$ aryl, and substituted or unsubstituted $C_3$-$C_{40}$ heteroaryl;

represents the connection location.

In the present disclosure, "$C_5$-$C_{40}$ aryl" includes monocyclic aromatic hydrocarbon group, and also includes fused ring aromatic hydrocarbon group, and may be, for example, selected from one or more of the following aromatic hydrocarbon groups: phenyl, and polycyclic aryl groups, such as biphenyl, 9,9-fluorenyl, terphenyl, naphthyl, anthracenyl, phenanthryl, 9,10-benzophenanthrenyl, 1,2-benzophenanthrenyl, acenaphthylenyl, perylenyl, pyrenyl, and indenyl.

"C3-C40 heteroaryl" may be, for example, selected from one or more of furyl, thienyl, pyrrolyl, oxazolyl, thiazolyl, pyrazolyl, pyranyl, imidazolyl, pyridyl, pyrazinyl, pyrimidinyl, 1,3,4-oxadiazolyl, 1,2,4-triazolyl, 1,3,5-triazinyl, indolyl, benzimidazolyl, dibenzofuranyl, dibenzothiophenyl, carbazolyl, quinolyl, quinoxalinyl, phenanthrolinyl, phenazinyl, and pyridazinyl.

In the present disclosure, without special explanation, the substitution in the "substituted . . . " may be any one or more of $C_1$-$C_{10}$ alkyl, $C_3$-$C_{10}$ cycloalkyl, $C_2$-$C_{10}$ alkenyl, $C_1$-$C_6$ alkoxyl, halogen, cyano, $C_6$-$C_{30}$ monocyclic aromatic hydrocarbon or fused ring aromatic hydrocarbon group, and $C_3$-$C_{30}$ monocyclic heteroaromatic hydrocarbon or fused ring heteroaromatic hydrocarbon group.

"$C_6$-$C_{30}$ monocyclic aromatic hydrocarbon or fused ring aromatic hydrocarbon group" may be, for example, phenyl, and polycyclic aryl groups, such as, biphenyl, 9,9-fluorenyl, terphenyl, naphthyl, anthracenyl, phenanthryl, 9,10-benzophenanthrenyl, 1,2-benzophenanthrenyl, acenaphthylenyl, perylenyl, pyrenyl, and indenyl.

"$C_3$-$C_{30}$ monocyclic heteroaromatic hydrocarbon or fused ring heteroaromatic hydrocarbon group" may be, for example, furyl, thienyl, pyrrolyl, oxazolyl, thiazolyl, pyrazolyl, pyranyl, imidazolyl, pyridyl, pyrazinyl, pyrimidinyl, 1,3,4-oxadiazolyl, 1,2,4-triazolyl, 1,3,5-triazinyl, indolyl, benzimidazolyl, dibenzofuranyl, dibenzothiophenyl, carbazolyl, quinolyl, quinoxalinyl, phenanthrolinyl, phenazinyl, and pyridazinyl.

In the present disclosure, under the condition that there is no clear indication of the connection position or representation of the connection position by #, various groups and substitutions may be connected to one another at any position as long as the corresponding compound in such connection can be prepared.

According to one embodiment of the present disclosure, $X_1$-$X_3$ are all C atoms.

According to one embodiment of the present disclosure, $R_1$-$R_9$ are each independently selected from substituted or unsubstituted phenyl.

According to one embodiment of the present disclosure, A is the structure shown in Formula (II-1), or Formula (II-2),

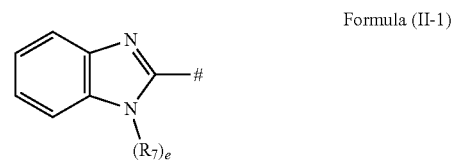

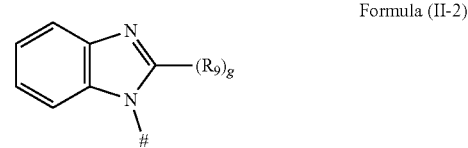

In one embodiment, $R_7$ and $R_9$ are each independently selected from $C_1$-$C_{12}$ alkyl, substituted or unsubstituted $C_5$-$C_{40}$ aryl, substituted or unsubstituted $C_3$-$C_{40}$ heteroaryl; and e and g are each independently selected from 0, or 1;

represents the connection location.

According to one embodiment of the present disclosure, $R_7$ and $R_9$ are each independently selected from substituted or unsubstituted phenyl.

According to one embodiment of the present disclosure, $L_2$ is identical to $L_3$, and s is identical to t.

According to one embodiment of the present disclosure, r, s, and t are all 0.

According to one embodiment of the present disclosure, one of a to f is 1, and the others are 0.

According to one embodiment of the present disclosure, g is 1.

According to one embodiment of the present disclosure, one of p and q is 1, and the other is 0.

According to one embodiment of the present disclosure, $L_1$-$L_3$ are each independently selected from one or more of the following groups:

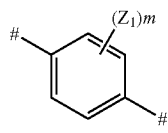

Chemical Formula 2-1

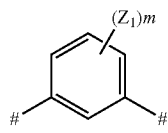

Chemical Formula 2-2

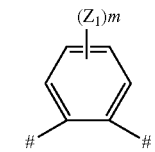

Chemical Formula 2-3

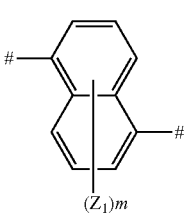

Chemical Formula 2-4

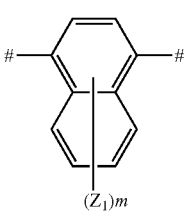

Chemical Formula 2-5

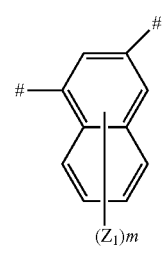

Chemical Formula 2-6

-continued

Chemical Formula 2-7

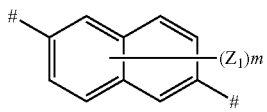

Chemical Formula 2-8

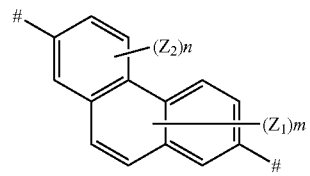

Chemical Formula 2-9

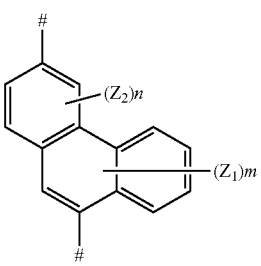

Chemical Formula 2-10

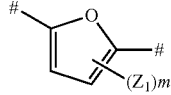

Chemical Formula 2-11

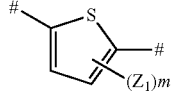

Chemical Formula 2-12

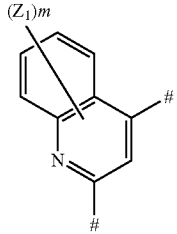

Chemical Formula 2-13

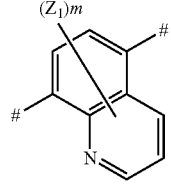

Chemical Formula 2-14

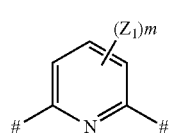

Chemical Formula 2-15

Chemical Formula 2-16
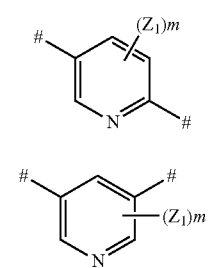
Chemical Formula 2-17
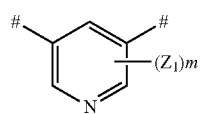
Chemical Formula 2-18
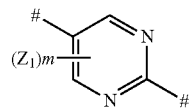
Chemical Formula 2-19
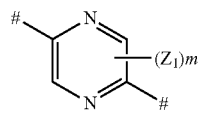
Chemical Formula 2-20
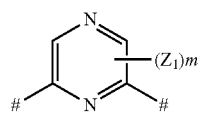
Chemical Formula 3-1
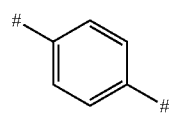
Chemical Formula 3-2
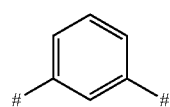
Chemical Formula 3-3
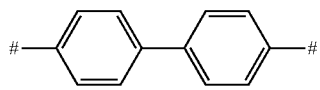
Chemical Formula 3-4
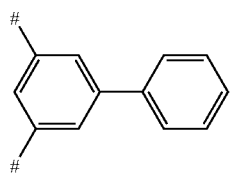
Chemical Formula 3-5
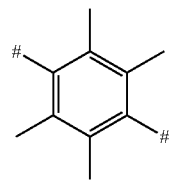
Chemical Formula 3-6
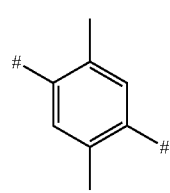
Chemical Formula 3-7
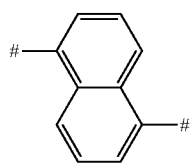
Chemical Formula 3-8
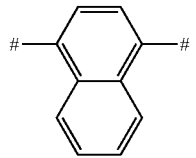
Chemical Formula 3-9
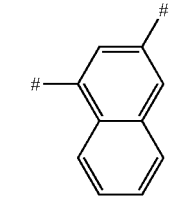
Chemical Formula 3-10
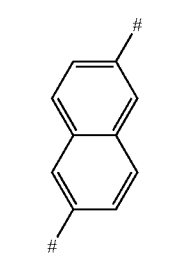
Chemical Formula 3-11
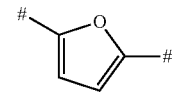
Chemical Formula 3-12
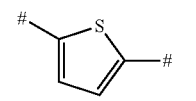
Chemial Formula 3-13
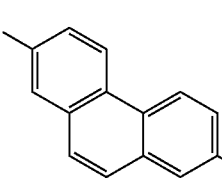
Chemical Formula 3-14
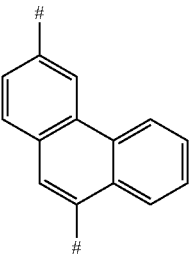
Chemical Formula 3-15
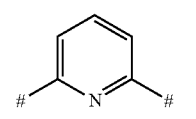

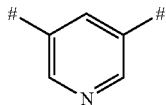

Chemical Formula 3-16

In one embodiment, $Z_1$ and $Z_2$ are each independently selected from any one or more of $C_1$-$C_{10}$ alkyl, $C_3$-$C_{10}$ cycloalkyl, $C_2$-$C_{10}$ alkenyl, $C_1$-$C_6$ alkoxyl, halogen, cyano, $C_6$-$C_{30}$ monocyclic aromatic hydrocarbon or fused ring aromatic hydrocarbon group, and $C_3$-$C_{30}$ monocyclic heteroaromatic hydrocarbon or fused ring heteroaromatic hydrocarbon group; m and n are each independently selected from 0, 1, or 2; and # represents the connection location.

According to one embodiment of the present disclosure, $Z_1$ and $Z_2$ are each independently selected from $C_6$-$C_{30}$ monocyclic aryl or polycyclic aryl.

According to one embodiment of the present disclosure, the compound has the structure shown in Formula (I-1),

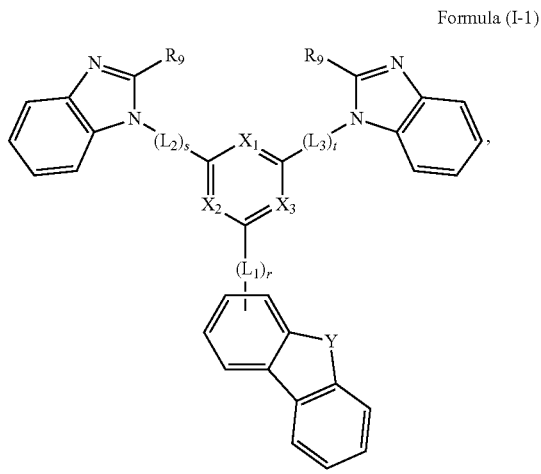

Formula (I-1)

In one embodiment, $X_1$-$X_3$ are each independently selected from an N atom, or a C atom; and $L_1$-$L_3$ are each independently selected from substituted or unsubstituted $C_5$-$C_{40}$ aryl, substituted or unsubstituted $C_3$-$C_{40}$ heteroaryl; r, s, and t are each independently selected from 0, or 1; and Y is selected from an N atom, an O atom, or an S atom.

According to one embodiment of the present disclosure, r, s, and t are all 0.

According to one embodiment of the present disclosure, $R_1$-$R_9$ are each independently selected from any one or more of substituted or unsubstituted $C_5$-$C_{40}$ aryl, substituted or unsubstituted $C_3$-$C_{40}$ heteroaryl; and the substituent is selected from any one or more of $C_1$-$C_{10}$ alkyl, $C_3$-$C_{10}$ cycloalkyl, $C_2$-$C_{10}$ alkenyl, $C_1$-$C_6$ alkoxyl, halogen, cyano, $C_6$-$C_{30}$ monocyclic aromatic hydrocarbon or fused ring aromatic hydrocarbon group, and $C_3$-$C_{30}$ monocyclic heteroaromatic hydrocarbon or fused ring heteroaromatic hydrocarbon group.

According to an embodiment of the present disclosure, the compound is selected from any one of HB01 to HB51.

According to one embodiment of the present disclosure, the compound is selected from any one of HB01, HB18, HB25, HB45, and HB48.

According to another embodiment of the present disclosure, there is provided an organic electroluminescent device including a first electrode and a second electrode, and an organic functional layer located between the first electrode and the second electrode, and the organic functional layer includes a hole-blocking layer, and the transport material of the hole-blocking layer includes the compound according to the present disclosure.

According to an embodiment of the present disclosure, the organic electroluminescent device includes a substrate, an anode and a cathode which are oppositely disposed, and an organic functional layer located between the anode and the cathode, and the organic functional layer including an electron injection layer, an electron transport layer, an light emitting layer, a hole transport layer, and a hole injection layer.

An organic electroluminescent device according to an embodiment of the present disclosure, as shown in FIG. 1, includes a substrate 1, an ITO anode 2, a hole injection layer 3, a first hole transport layer 4, a second hole transport layer 5, an light emitting layer 6, a hole-blocking layer 7, an electron transport layer 8, an electron injection layer 9, and a cathode 10 which are sequentially disposed.

The organic electroluminescent device structure may be a single light emitting layer or a multiple light emitting layer.

Among them, the substrate can use a substrate in a conventional organic electroluminescent device, such as glass or plastic. The anode can be made of a transparent highly-conductive material, such as indium tin oxide (ITO), indium zinc oxide (IZO), tin dioxide ($SnO_2$), or zinc oxide (ZnO).

The hole injection material (Hole Injection Material, HIM for short) of the hole injection layer is required to have high thermal stability (high Tg) and a smaller barrier with the anode, and can be vacuum-deposited to form a pinhole-free film. Commonly used HTMs are aromatic polyamines, mainly triarylamine derivatives.

The hole transport material (Hole Transport Material, HTM for short) of the hole transport layer is required to have high thermal stability (high Tg) and higher hole transporting capability, and can be vacuum-deposited to form a pinhole-free film. Commonly used HTMs are aromatic polyamines, mainly triarylamine derivatives.

The organic light emitting layer includes a host material (host) and a guest material, and the guest material is a luminescent material, such as a dye, and the host material is required to have the following characteristics: reversible electrochemical oxidation-reduction potential, HOMO energy level and LUMO energy level matched with adjacent hole transport layer and electron transport layer, good and matched hole and electron transport capability, good and high thermal stability and film formation, and suitable singlet or triplet energy gap for controlling a good energy transfer of excitons between the light emitting layer and corresponding fluorescent dye or phosphorescent dye. The luminescent material of the organic light emitting layer, taking a dye as an example, is required to have the following characteristics: having high fluorescence or phosphorescence quantum efficiency; good overlapping of the absorption spectrum of the dye with the emission spectrum of the host, that is, the host and the dye are adapted in terms of energy so that the energy can effectively transferred from the host to the dye; the emission peaks of red, green, and blue are as narrow as possible to obtain good color purity; and good stability to perform evaporation.

The electron transport material (Electron Transport Material, ETM for short) of the electron transport layer requires ETM to have reversible and sufficiently high electrochemical reduction potential and appropriate values of HOMO energy level and LUMO (Lowest Unoccupied Molecular Orbital) energy level that make the electrons injected better, and may have hole-blocking capability, higher electron transport capability, and good film formation and thermal stability. ETM is generally an aromatic compound having a conjugated plane having an electron deficient structure. The electron transport layer adopts Alq3 (8-hydroxyquinoline aluminum) or TAZ (3-phenyl-4-(1'-naphthyl)-5-benzene-1, 2,4-triazole) or TPBi (1,3,5-tris(N-phenyl-2-benzimidazole) benzene), or a combination of any two of these three materials.

In the present disclosure, the organic electroluminescent device is manufactured by forming an anode (the first electrode) on a transparent or opaque smooth substrate, forming an organic functional layer on the anode, and forming a cathode (the second electrode) on the organic functional layer. The organic functional layer can be formed by a known film formation method such as vapor deposition, sputtering, spin coating, dipping, or ion plating.

According to another embodiment of the present disclosure, there is provided a display equipment including the organic electroluminescent device according to the present disclosure.

Figure 2:
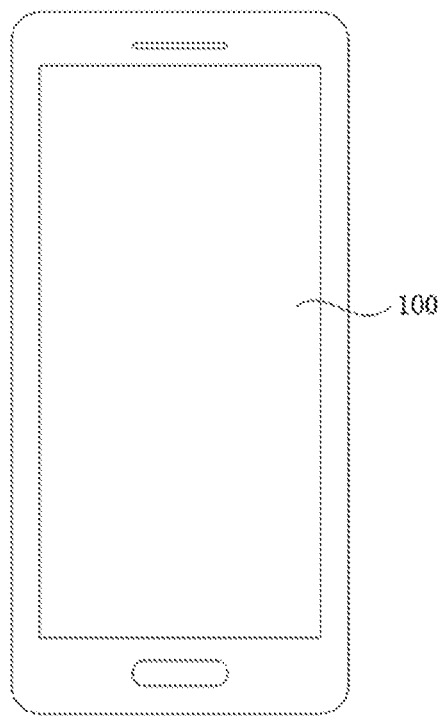
FIG. 2 is the schematic diagram of the mobile phone display screen.

According to an embodiment of the present disclosure, the display equipment may be a mobile phone, a computer, a liquid crystal television, a smart watch, a smart car, a VR or AR helmet, etc., which is not specifically limited in the present disclosure. FIG. 2 is a schematic diagram of a mobile phone display screen, and 100 represents a display screen.

Thus, it can be seen that there are many optional factors for the compound, the organic electroluminescent device, and the display equipment according to the present disclosure, and different embodiments can be combined according to the claims of the present disclosure. The embodiments of the present disclosure are only intended to be a detailed description of the present disclosure, and are not intended to limit the present disclosure. The present disclosure will now be further described in combination with an organic electroluminescent device containing a compound of the present disclosure as an embodiment.

Preparation Example 1

Preparation of Compound HB01

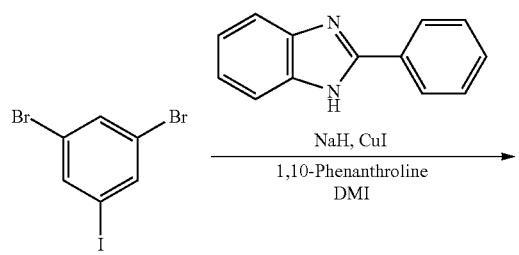

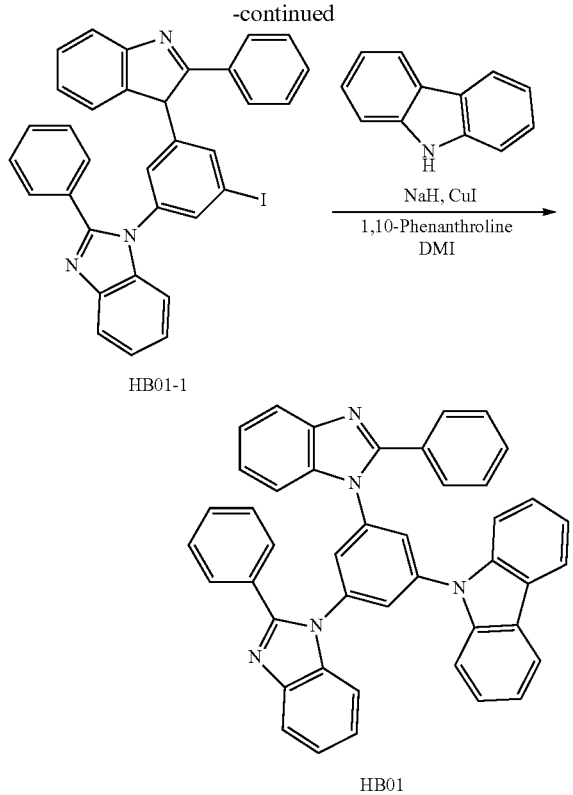

The preparation method is as follows:

(1) Preparation of Compound HB01-1:

in a 250 mL round bottom flask, 1,3-dibromo-5-iodobenzene (10 mmol), copper iodide (15 mmol), potassium tert-butoxide (65 mmol), 1,2-diaminocyclohexane (12 mmol), and 2-phenyl-1H-benzimidazole (25 mmol) were added to anhydrous 1,4-dioxane (150 mL). The mixture was refluxed for 48 h under nitrogen atmosphere. The resultant intermediate was cooled to room temperature, added to water, and then filtered by diatomite pad. The filtrate was extracted with dichloromethane, washed with water, and dried with anhydrous magnesium sulfate. After being filtered and evaporated, the crude product was purified by silica gel column chromatography to obtain the intermediate product HB01-1.

(2) Preparation of Compound HB01:

in a 250 mL round bottom flask, the intermediate product HB01-1, copper iodide (15 mmol), potassium tert-butoxide (65 mmol), 1,2-diaminocyclohexane (12 mmol), and 9H-carbazole (25 mmol) were added to anhydrous 1,4-dioxane (150 mL). The mixture was refluxed for 48 h under nitrogen atmosphere. The resultant intermediate was cooled to room temperature, added to water, and then filtered by diatomite pad. The filtrate was extracted with dichloromethane, washed with water, and dried with anhydrous magnesium sulfate. After being filtered and evaporated, the crude product was purified by silica gel column chromatography to obtain the intermediate product HB01.

Elemental analysis structure of Compound HB01 (molecular formula of $C_{44}H_{29}N_5$): theoretical value: C, 84.19; H, 4.66; N, 11.16. Test value: C, 84.18; H, 4.67; N, 11.16. ESI-MS (m/z)(M$^+$) obtained by liquid phase mass spectrometry: theoretical value: 627.24, test value: 627.73.

Preparation Example 2

Preparation of Compound HB18

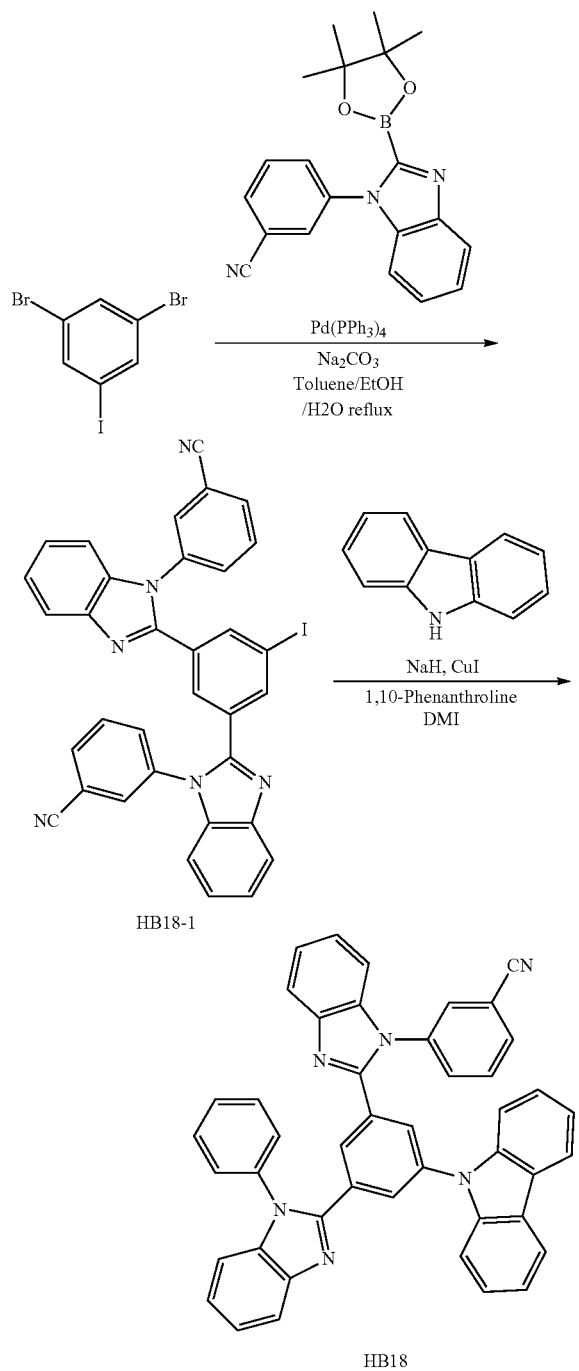

The preparation method is as follows:

(1) Preparation of Compound HB18-1 in a 250 mL round bottom flask, 1,3-dibromo-5-iodobenzene (10 mmol), 1-benzonitrile-2-borate-benzimidazole (22 mmol), and Pd(PPh$_3$)$_4$ (0.3 mmol) were added to the mixture of toluene (30 mL)/ethanol (20 mL) and aqueous solution (10 mL) of potassium carbonate (12 mmol). The mixture was refluxed for 12 h under nitrogen atmosphere. The resultant mixture was cooled to room temperature, added to water, and then filtered by diatomite pad. The filtrate was extracted with dichloromethane, washed with water, and dried with anhydrous magnesium sulfate. After being filtered and evaporated, the crude product was purified by silica gel column chromatography to obtain the final product HB18-1.

(2) Preparation of Compound HB18 in a 250 mL round bottom flask, the intermediate product HB18-1, copper iodide (15 mmol), potassium tert-butoxide (65 mmol), 1,2-diaminocyclohexane (12 mmol), and 9H-carbazole (25 mmol) were added to anhydrous 1,4-dioxane (150 mL). The mixture was refluxed for 48 h under nitrogen atmosphere. The resultant intermediate was cooled to room temperature, added to water, and then filtered by diatomite pad. The filtrate was extracted with dichloromethane, washed with water, and dried with anhydrous magnesium sulfate. After being filtered and evaporated, the crude product was purified by silica gel column chromatography to obtain intermediate product HB18.

Elemental analysis structure of Compound HB18 (molecular formula of $C_{46}H_{27}N_7$): theoretical value: C, 81.52; H, 4.02; N, 14.47. Test value: C, 81.52; H, 4.02; N, 14.47. ESI-MS (m/z)(M$^+$) obtained by liquid phase mass spectrometry: theoretical value: 677.23, test value: 677.75.

Preparation Example 3

Preparation of Compound HB25

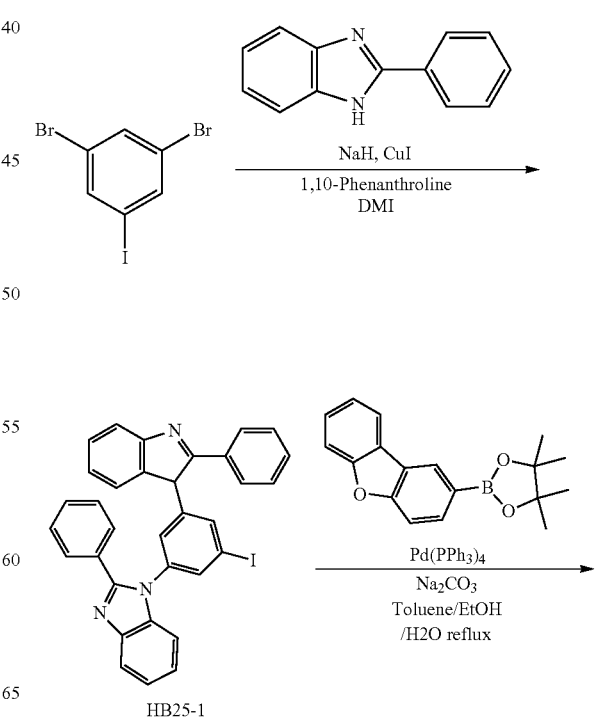

-continued

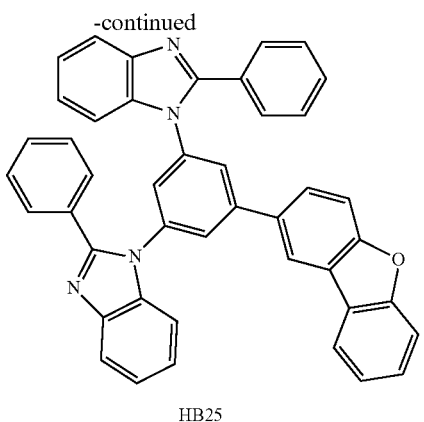

HB25

The preparation method is as follows:
(1) Preparation of Compound HB25-1 in a 250 mL round bottom flask, 1,3-dibromo-5-iodobenzene (10 mmol), copper iodide (15 mmol), potassium tert-butoxide (65 mmol), 1,2-diaminocyclohexane (12 mmol), and 2-phenyl-1H-benzimidazole (25 mmol) were added to anhydrous 1,4-dioxane (150 mL). The mixture was refluxed for 48 h under nitrogen atmosphere. The resultant intermediate was cooled to room temperature, added to water, and then filtered by diatomite pad. The filtrate was extracted with dichloromethane, washed with water, and dried with anhydrous magnesium sulfate. After being filtered and evaporated, the crude product was purified by silica gel column chromatography to obtain the intermediate product HB25-1.

(2) Preparation of Compound HB25 in a 250 mL round bottom flask, the intermediate product HB25-1, 3-borate-dibenzofuran (22 mmol), and Pd(PPh$_3$)$_4$ (0.3 mmol) were added to the mixture of toluene (30 mL)/ethanol (20 mL) and the aqueous solution (10 mL) of potassium carbonate (12 mmol). The mixture was refluxed for 12 h under nitrogen atmosphere. The resultant mixture was cooled to room temperature, added to water, and then filtered by diatomite pad. The filtrate was extracted with dichloromethane, washed with water, and dried with anhydrous magnesium sulfate. After being filtered and evaporated, the crude product was purified by silica gel column chromatography to obtain the final product HB25.

Elemental analysis structure of Compound HB25 (molecular formula of $C_{44}H_{28}N_4O$): theoretical value: C, 84.06; H, 4.49; N, 8.91; O, 2.54. Test value: C, 84.06; H, 4.48; N, 8.92; O, 2.54. ESI-MS (m/z)(M$^+$) obtained by liquid phase mass spectrometry: theoretical value: 628.23, test value: 628.72.

Preparation Example 4

Preparation of Compound HB45

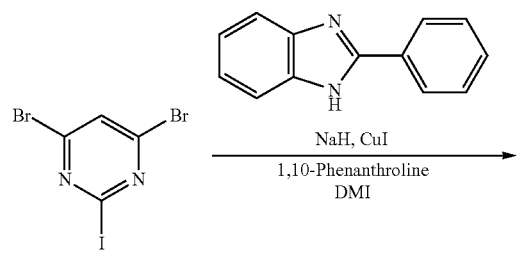

-continued

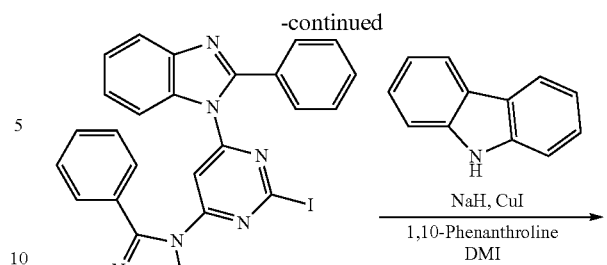

HB45-1

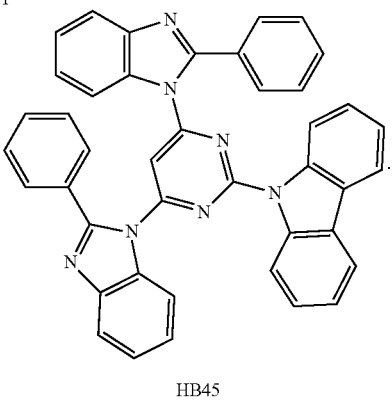

HB45

The preparation method is as follows:
(1) Preparation of Compound HB45-1 in a 250 mL round bottom flask, 4,6-dibromo-2-iodopyrimidine (10 mmol), copper iodide (15 mmol), potassium tert-butoxide (65 mmol), 1,2-diaminocyclohexane (12 mmol), and 2-phenyl-1H-benzimidazole (25 mmol) were added to anhydrous 1,4-dioxane (150 mL). The mixture was refluxed for 48 h under nitrogen atmosphere. The resultant intermediate was cooled to room temperature, added to water, and then filtered by diatomite pad. The filtrate was extracted with dichloromethane, washed with water, and dried with anhydrous magnesium sulfate. After being filtered and evaporated, the crude product was purified by silica gel column chromatography to obtain the intermediate product HB45-1.

(2) Preparation of Compound HB45 a 250 mL round bottom flask, the intermediate product HB45-1, copper iodide (15 mmol), potassium tert-butoxide (65 mmol), 1,2-diaminocyclohexane (12 mmol), and 9H-carbazole (25 mmol) were added to anhydrous 1,4-dioxane (150 mL). The mixture was refluxed for 48 h under nitrogen atmosphere. The resultant intermediate was cooled to room temperature, added to water, and then filtered by diatomite pad. The filtrate was extracted with dichloromethane, washed with water, and dried with anhydrous magnesium sulfate. After being filtered and evaporated, the crude product was purified by silica gel column chromatography to obtain intermediate product HB45.

Elemental analysis structure of Compound HB45 (molecular formula of $C_{42}H_{27}N_7$): theoretical value: C, 80.11; H, 4.32; N, 15.57. Test value: C, 80.11; H, 4.32; N, 15.57. ESI-MS (m/z)(M$^+$) obtained by liquid phase mass spectrometry: theoretical value: 629.23, test value: 629.71.

Preparation Example 5

Preparation of Compound HB48

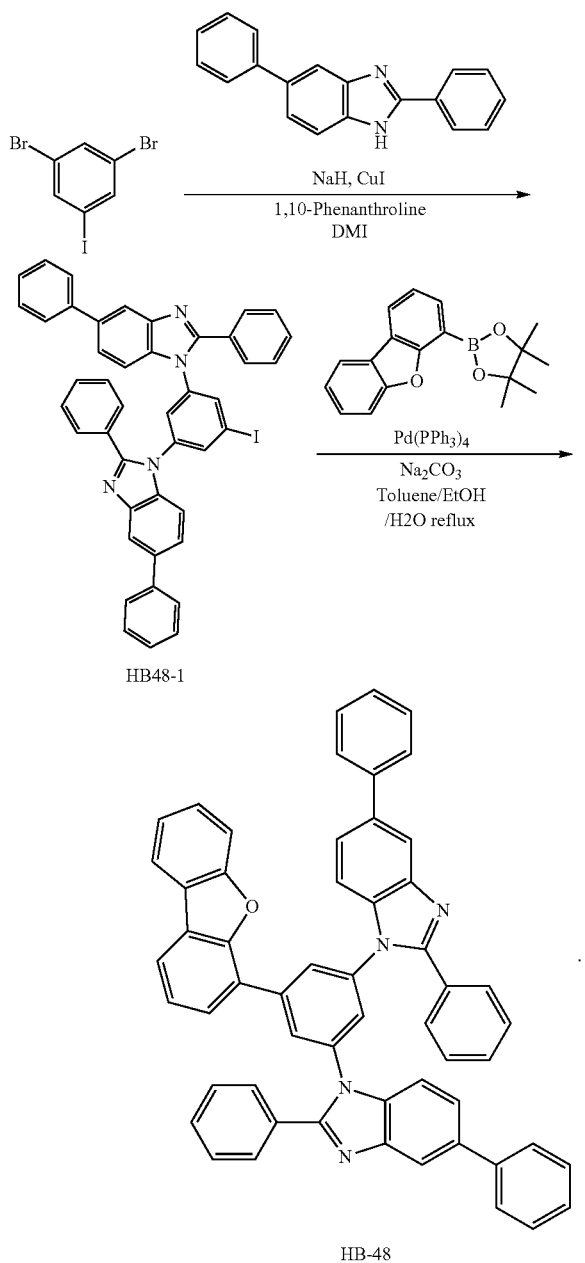

The preparation method is as follows:

(1) Preparation of Compound HB48-1 in a 250 mL round bottom flask, 1,3-dibromo-5-iodobenzene (10 mmol), copper iodide (15 mmol), potassium tert-butoxide (65 mmol), 1,2-diaminocyclohexane (12 mmol), and 2,5-diphenyl-1H-benzimidazole (25 mmol) were added to anhydrous 1,4-dioxane (150 mL). The mixture was refluxed for 48 h under nitrogen atmosphere. The resultant intermediate was cooled to room temperature, added to water, and then filtered by diatomite pad. The filtrate was extracted with dichloromethane, washed with water, and dried with anhydrous magnesium sulfate. After being filtered and evaporated, the crude product was purified by silica gel column chromatography to obtain the intermediate product HB48-1.

(2) Preparation of Compound HB48 in a 250 mL round bottom flask, the intermediate product HB48-1, 1-borate-dibenzofuran (22 mmol), and Pd(PPh$_3$)$_4$ (0.3 mmol) were added to the mixture of toluene (30 mL)/ethanol (20 mL) and the aqueous solution (10 mL) of potassium carbonate (12 mmol). The mixture was refluxed for 12 h under nitrogen atmosphere. The resultant mixture was cooled to room temperature, added to water, and then filtered by diatomite pad. The filtrate was extracted with dichloromethane, washed with water, and dried with anhydrous magnesium sulfate. After being filtered and evaporated, the crude product was purified by silica gel column chromatography to obtain the final product HB48.

Elemental analysis structure of Compound HB48 (molecular formula of $C_{56}H_{36}N_4O$): theoretical value: C, 86.13; H, 4.65; N, 7.17; O, 2.05. Test value: C, 86.13; H, 4.66; N, 7.16; O, 2.05. ESI-MS (m/z)(M$^+$) obtained by liquid phase mass spectrometry: theoretical value: 780.29, test value: 780.91.

For other compounds, similar synthetic methods were also used.

Performance Testing (1) Simulation Calculation of Compounds the compounds obtained from Preparation examples 1-5 are subject to simulation calculation as follows:

the difference between singlet and triplet energy level of the organic materials can be completed by Guassian 09 software (Guassian Inc). The detailed simulation method of the energy level difference ΔEst refers to J. Chem. Theory Comput., 2013, DOI: 10.1021/ct400415r. The optimization and excitation of molecular structure can be completed by the TD-DFT method "B3LYP" and the base group "6-31 g(d)", and the Tg is measured by differential scanning calorimetry. The results of the compounds prepared in Preparation examples 1-5 are shown in Table 1.

TABLE 1

| Example Number | Compound Number | HOMO (ev) | LUMO (ev) | Eg (ev) | E$_T$ (ev) | Tg (° C.) |
|---|---|---|---|---|---|---|
| Example 1 | HB01 | −5.926 | −2.435 | 3.491 | 3.015 | 132 |
| Example 2 | HB18 | −5.957 | −2.508 | 3.449 | 3.008 | 138 |
| Example 3 | HB25 | −6.078 | −2.411 | 3.667 | 3.019 | 134 |
| Example 4 | HB45 | −5.949 | −2.526 | 3.423 | 3.001 | 135 |
| Example 5 | HB48 | −6.046 | −2.405 | 3.641 | 3.016 | 136 |

As can be seen from Table 1, the HOMO energy level of all compounds in the examples of the present disclosure is greater than 5.9 eV, indicating that the material has a weaker electron donating capability, which can effectively block holes from passing through the light emitting layer, so that the holes and electrons can recombine in the light emitting layer, thus effectively improving the recombination efficiency. The triplet energy level of all compounds in the examples of the present disclosure is greater than 3.0 eV, indicating that the material can effectively block the recombined excitons from passing through the light emitting layer to the electron transport layer, and restrict the excitons in the light emitting region, thus effectively improving the optical radiation efficiency of the excitons, and widening the light emitting region. The glass transition temperature of all compounds in the examples of the present disclosure is greater than 130° C., indicating that the thermal stability of the compound is good, and the degradation and deterioration of stability of the material will not be caused during the evaporation and operation of the device. In conclusion, the compound of the present disclosure is beneficial to widen the light emitting region, improving the luminescent efficiency and service life of the device.

(2) Performance of the organic electroluminescent device

Example 6 the example provides an OLED display panel. As shown in FIG. 1, the OLED display panel includes: a substrate 1, an ITO anode 2, a hole injection layer 3, a first hole transport layer 4, and a second hole transport layer 5, a light emitting layer 6, a hole-blocking layer 7, an electron transport layer 8, an electron injecting layer 9, and a cathode 10 (aluminum electrode), and the thickness of the ITO anode 2 is 10 nm, and the thickness of the hole injection layer 3 is 5 nm, the thickness of the first hole transport layer 4 is 50 nm, the thickness of the second hole transport layer 5 is 10 nm, the thickness of the light emitting layer 6 is 20 nm, the thickness of the hole-blocking layer 7 is 5 nm, the thickness of the electron transport layer 8 is 20 nm, the thickness of the electron injection layer 9 is 1 nm, and the thickness of the aluminum electrode 10 is 15 nm. The arrow indicates the direction of light.

The preparation steps of the OLED display panel are as follows:

1) The glass substrate 1 is cut into a size of 50 mm×50 mm×0.7 mm, subject to ultrasonic treatment in isopropyl alcohol and deionized water for 30 minutes, respectively, and then exposed to ozone for about 10 minutes for cleaning; the obtained glass substrate having ITO anode 2 is mounted to a vacuum deposition equipment;

2) The material HAT-CN of the hole injection layer is deposited on the ITO anode layer 2 by vacuum deposition method at a vacuum degree of $2\times10^{-6}$ Pa to a thickness of 5 nm as the hole injection layer 3;

3) The material N,N'-diphenyl-N,N'-(1-naphthyl)-1,1'-biphenyl-4,4'-diamine (α-NPD) of the first hole transport layer 2 is vacuum-deposited on the hole injection layer 3 to a thickness of 50 nm as the first hole transport layer 4;

4) The material 1,3-dicarbazol-9-ylbenzene (mCP) of the second hole transport layer 5 is vacuum-deposited on the first hole transport layer 4 to a thickness of 10 nm as the second hole transport layer 5;

5) The light emitting layer 6 is co-deposited on the second hole transport layer 5 to a thickness of 20 nm, the host material of the light emitting layer 6 is CBP, and the guest material is Ir(piq)$_3$, with the mass ratio of the compound CBP to FIrpic of 97:3;

6) The hole-blocking layer 7 is vacuum-deposited on the light emitting layer 6 to a thickness of 5 nm, and the material of the hole-blocking layer 7 is HB01 prepared in the Preparation example 1;

7) The electron transport layer 8 is vacuum-deposited on the hole-blocking layer 7 to a thickness of 20 nm, and the material of the electron transport layer 8 is BPen;

8) The electron injection layer 9 is vacuum-deposited on the electron transport layer 8 to a thickness of 1 nm, and the material of the electron injection layer 9 is LiF;

9) An aluminum electrode is vacuum-deposited on the electron injection layer 9 to a thickness of 15 nm, and is used as the cathode 10.

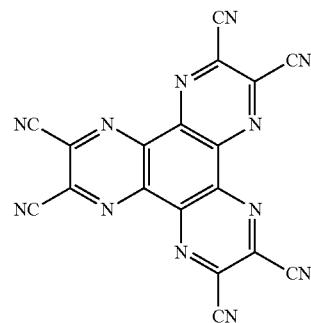

HAT-CN

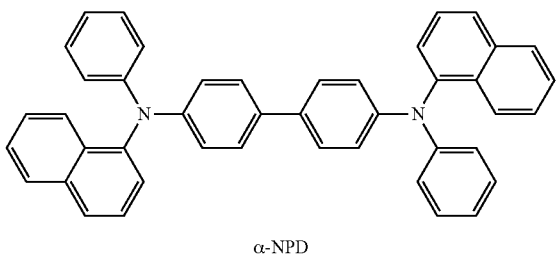

α-NPD

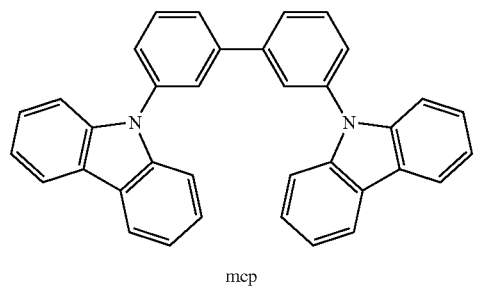

mcp

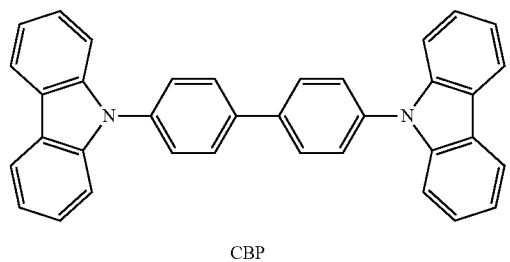

CBP

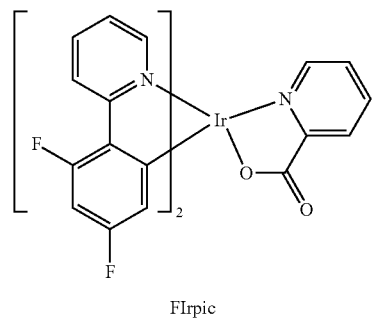

FIrpic

-continued

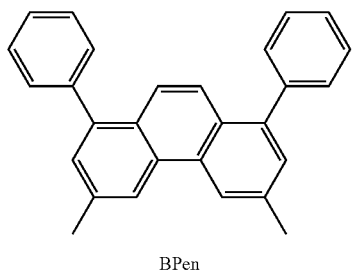

BPen

Example 7 the only difference from example 6 is that HB01 is replaced with HB18.

Example 8 the only difference from example 6 is that HB01 is replaced with HB25.

Example 9 the only difference from example 6 is that HB01 is replaced with HB45.

Example 10 the only difference from example 6 is that HB01 is replaced with HB48.

Comparative Example 1 the difference from example 6 is that HB01 is replaced with Compound M.

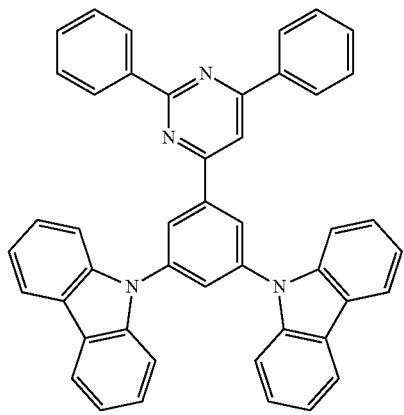 [SMILES: c1ccc(-c2cc(-c3cc(-n4c5ccccc5c5ccccc54)cc(-n4c5ccccc5c5ccccc54)c3)nc(-c3ccccc3)n2)cc1]

The structural formula of Compound M

The performance test results of the examples and comparative example are shown in Table 2.

TABLE 2

| | Hole-blocking Material | Driving Voltage V | Current Efficiency (E/CIEy) cd/A | Lifetime LT95 (@50 mA/cm$^2$) |
|---|---|---|---|---|
| Comparative Example 1 | M | 3.78 | 60.8 | 63 |
| Example 6 | HB01 | 3.65 | 67.5 | 75 |
| Example 7 | HB18 | 3.66 | 68.2 | 73 |
| Example 8 | HB25 | 3.62 | 68.4 | 72 |
| Example 9 | HB45 | 3.69 | 67.2 | 75 |
| Example 10 | HB48 | 3.67 | 69.7 | 70 |

As can be seen from Table 2, compared with the comparative example 1, the OLED display panel provided by the present disclosure has a lower driving voltage, higher luminescent efficiency and a longer service life, and the driving voltage is less than 3.70V, and is increased by about 3%; the luminescent efficiency (E/CIEy) is greater than 67Cd/A, and is increased by about 10%; the service life is over 70 h, and is increased by more than 12%. The above performances of the display panel are improved, mainly because of the material of the present disclosure, which has lower HOMO value and particularly high triplet energy level (more than 3.0 eV), can effectively block the hole reflow and prevent excitons passing through the light emitting layer, widen the light emitting region, improve the utilization rate and radiation efficiency of excitons, and reduce energy consumption caused by non-radiation. Meanwhile, the material has high glass transition temperature and good thermal stability, which is beneficial for prolonging the service life of the device.

The present disclosure has the following beneficial effects:

The compound provided in the present disclosure takes a nitrogen-containing aromatic heterocyclic ring as a parent ring, and is used in conjunction with benzimidazole and heterofluorene groups, so that the compound obtained has a relatively shallow HOMO value and LUMO value, which can better match with adjacent layers and improve the electron transport capability. The compound of the present disclosure has a lower HOMO energy level (all of which are close to −6.0 eV), which can effectively block the holes and restrict them in the light emitting region, and effectively recombined with electrons. The compound of the present disclosure has a higher triplet energy level (ET is all greater than 3.0 eV) which can effectively prevent the return of excitons and restrict them in the light emitting region, which is beneficial to widen the light emitting region and improving the luminescent efficiency. The compound of the present disclosure also has higher electron mobility, which ensures that electrons and holes can be evenly recombined in the light emitting layer, thus increasing the production rate of excitons; and the compound also has higher glass transition temperature and thermal decomposition temperature, and the glass transition temperature being greater than 130° C., which can avoid the influence of Joule heat generated by the device on the life and efficiency of the device; and the compound also has excellent film stability and uniformity, thus avoiding degradation or decay induced by light scattering or crystallization; and the compound has higher reduction potential which is convenient for electron transmission.

The compound can be used as the transport material for the organic electroluminescent device, which can effectively improve the electron mobility of the device, thus ensuring that the device has higher luminescent efficiency, longer service life, and lower driving voltage.

What is claimed is:

1. A compound, wherein the compound has a structure shown in Formula (I):

Formula (I)

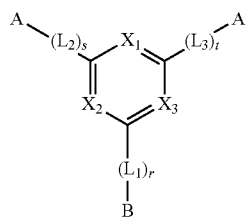

Formula (II)

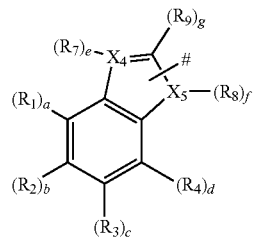

Formula (III)

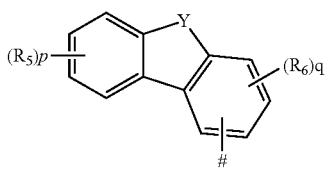

wherein $X_1$-$X_3$ are all C—H groups; r, s, t are selected from 0, 1, wherein at least one of r, s, t is equal to 1, and $L_1$-$L_3$ are each independently selected from any one or more of the following groups:

Chemical Formula 2-1

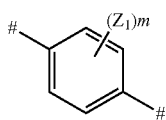

Chemical Formula 2-2

Chemical Formula 2-3

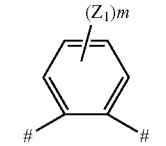

Chemical Formula 2-4

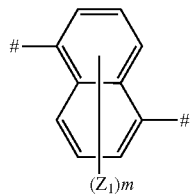

Chemical Formula 2-5

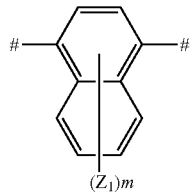

Chemical Formula 2-6

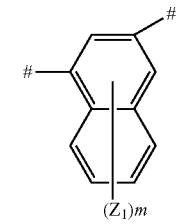

Chemical Formula 2-7

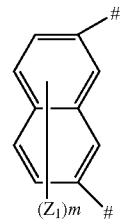

Chemical Formula 2-8

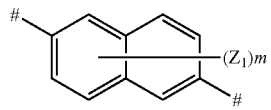

Chemical Formula 2-9

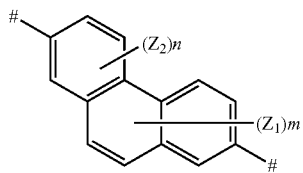

Chemical Formula 2-10

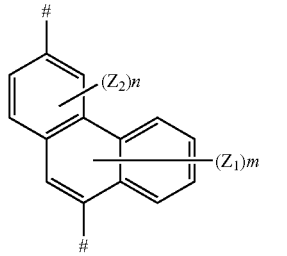

Chemical Formula 2-11

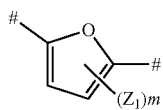

-continued

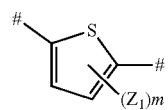
Chemical Formula 2-12

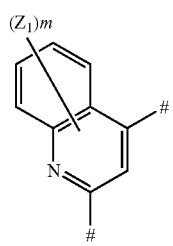
Chemical Formula 2-13

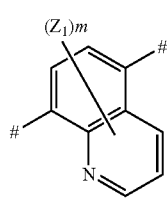
Chemical Formula 2-14

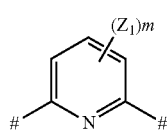
Chemical Formula 2-15

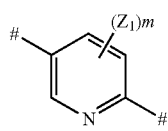
Chemical Formula 2-16

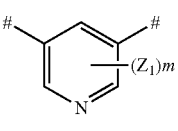
Chemical Formula 2-17

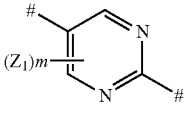
Chemical Formula 2-18

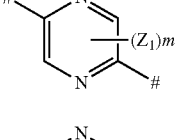
Chemical Formula 2-19

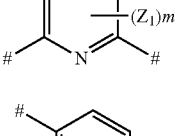
Chemical Formula 2-20

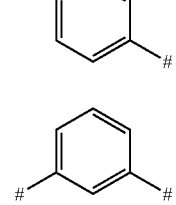
Chemical Formula 3-1

Chemical Formula 3-2

-continued

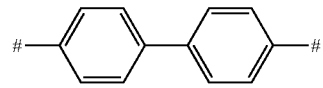
Chemical Formula 3-3

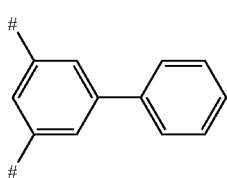
Chemical Formula 3-4

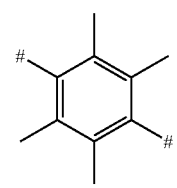
Chemical Formula 3-5

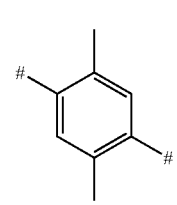
Chemical Formula 3-6

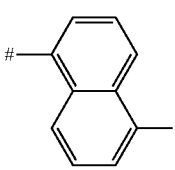
Chemical Formula 3-7

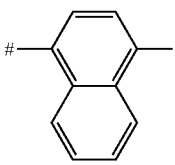
Chemical Formula 3-8

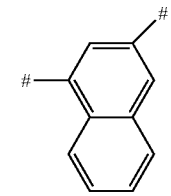
Chemical Formula 3-9

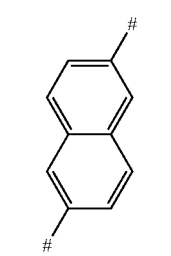
Chemical Formula 3-10

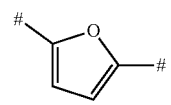
Chemical Formula 3-11

-continued

Chemical Formula 3-12

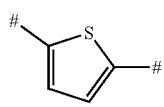

Chemical Formula 3-13

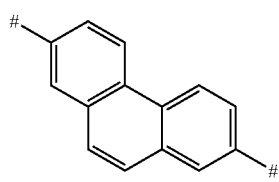

Chemical Formula 3-14

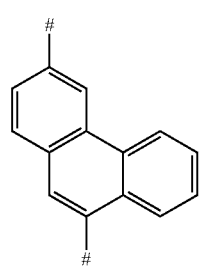

Chemical Formula 3-15

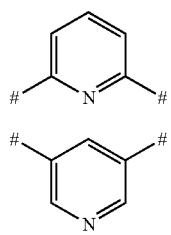

Chemical Formula 3-16 wherein $Z_1$ and $Z_2$ are each independently selected from any one or more of $C_1$-$C_{10}$ alkyl, $C_3$-$C_{10}$ cycloalkyl, $C_2$-$C_{10}$ alkenyl, $C_1$-$C_6$ alkoxyl, halogen, cyano, $C_6$-$C_{30}$ monocyclic heteroaromatic hydrocarbon or fused ring heteroaromatic hydrocarbon group, and $C_3$-$C_{30}$ monocyclic heteroaromatic hydrocarbon or fused ring heteroaromatic hydrocarbon group; m and n are each independently selected from 0, 1, or 2;

A is a structure shown in Formula (II), and B is a structure shown in Formula (III); in Formula (II), $X_4$ and $X_5$ are each independently selected from a C atom or an N atom, and at least one of them is an N atom; and a to f are each independently selected from 0, or 1, and g is 1;

in formula (III), Y is selected from an N atom, NPh, an O atom, or an S atom, when Y is an N atom, Formula (III) is joined to Formula (I) via the N atom; p and q are each independently selected from 1, 2, or 3;

$R_1$-$R_9$ are each independently selected from $C_1$-$C_{12}$ alkyl, substituted or unsubstituted $C_5$-$C_{40}$ aryl, and substituted or unsubstituted $C_3$-$C_{40}$ heteroaryl; and represents a connection location.

2. The compound according to claim 1, wherein $R_1$-$R_9$ are each independently selected from substituted or unsubstituted phenyl.

3. The compound according to claim 1, wherein A is the structure shown in Formula (II-1) or Formula (II-2),

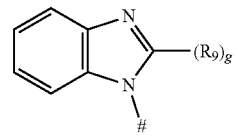

Formula (II-1)

wherein $R_9$ is selected from $C_1$-$C_{12}$ alkyl, substituted or unsubstituted $C_5$-$C_{40}$ aryl, substituted or unsubstituted $C_3$-$C_{40}$ heteroaryl; and g is 1; and represents the connection location.

4. The compound according to claim 3, wherein $R_9$ is selected from substituted or unsubstituted phenyl.

5. The compound according to claim 1, wherein $L_2$ is identical to $L_3$, and s is identical to t.

6. The compound according to claim 1, wherein one of a to f is 1, and others are 0.

7. The compound according to claim 1, wherein $Z_1$ and $Z_2$ are each independently selected from $C_6$-$C_{30}$ monocyclic heteroaromatic hydrocarbon or fused ring heteroaromatic hydrocarbon group.

8. The compound according to claim 1, wherein the compound has the structure shown in Formula (I-1),

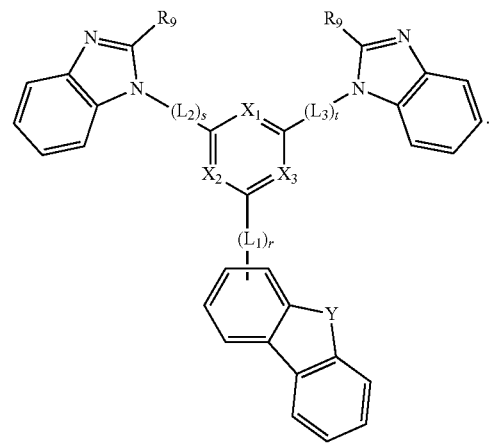

Formula (I-1)

wherein $X_1$-$X_3$ are all C—H groups; r, s, t are selected from 0, 1, wherein at least one of r, s, t is equal to 1, and $L_1$-$L_3$ are each independently selected from any one or more of the following groups:

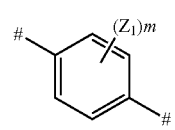

Chemical Formula 2-1

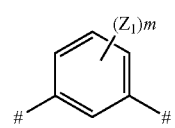

Chemical Formula 2-2

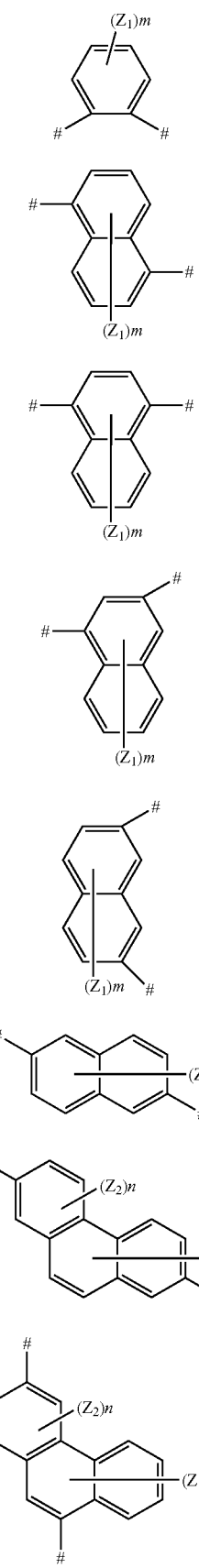
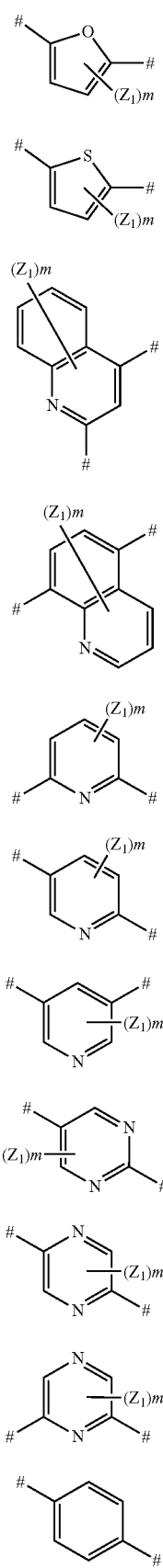
Chemical Formula 2-3
Chemical Formula 2-4
Chemical Formula 2-5
Chemical Formula 2-6
Chemical Formula 2-7
Chemical Formula 2-8
Chemical Formula 2-9
Chemical Formula 2-10
Chemical Formula 2-11
Chemical Formula 2-12
Chemical Formula 2-13
Chemical Formula 2-14
Chemical Formula 2-15
Chemical Formula 2-16
Chemical Formula 2-17
Chemical Formula 2-18
Chemical Formula 2-19
Chemical Formula 2-20
Chemical Formula 3-1

-continued

Chemical Formula 3-2

Chemical Formula 3-3

Chemical Formula 3-4

Chemical Formula 3-5

Chemical Formula 3-6

Chemical Formula 3-7

Chemical Formula 3-8

Chemical Formula 3-9

Chemical Formula 3-10

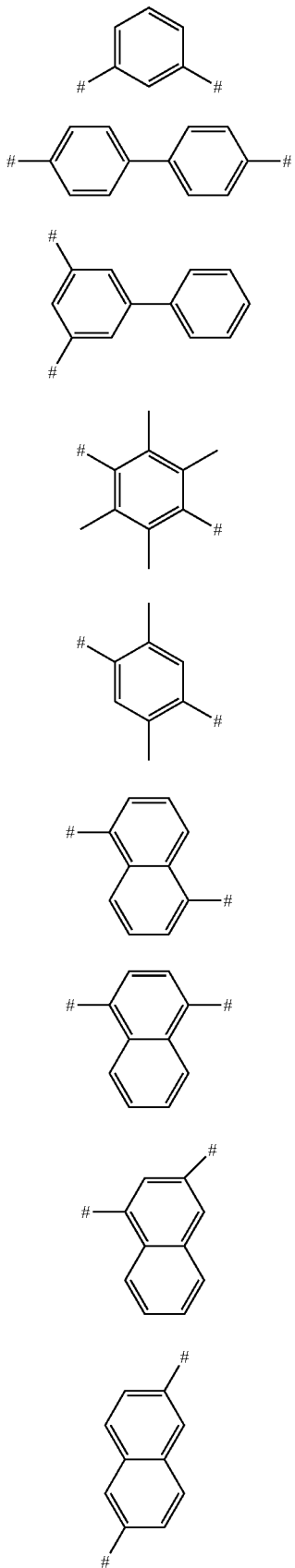

-continued

Chemical Formula 3-11

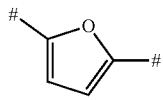

Chemical Formula 3-12

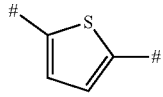

Chemical Formula 3-13

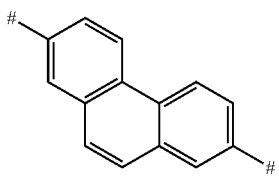

Chemical Formula 3-14

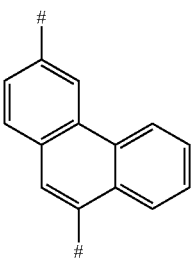

Chemical Formula 3-15

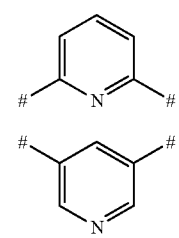

Chemical Formula 3-16

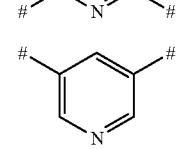

wherein $Z_1$ and $Z_2$ are each independently selected from any one or more of $C_1$-$C_{10}$ alkyl, $C_3$-$C_{10}$ cycloalkyl, $C_2$-$C_{10}$ alkenyl, $C_1$-$C_6$ alkoxyl, halogen, cyano, $C_6$-$C_{30}$ monocyclic heteroaromatic hydrocarbon or fused ring heteroaromatic hydrocarbon group, and $C_3$-$C_{30}$ monocyclic heteroaromatic hydrocarbon or fused ring heteroaromatic hydrocarbon group; m and n are each independently selected from 0, 1, or 2; and Y is selected from an N atom, NPh, an O atom, or an S atom, when Y is an N atom, Formula (III) is joined to Formula (I) via the N atom.

9. The compound according to claim 8, wherein $Z_1$ and $Z_2$ are each independently selected from $C_6$-$C_{30}$ monocyclic heteroaromatic hydrocarbon or fused ring heteroaromatic hydrocarbon group.

10. The compound according to claim 1, wherein $R_1$-$R_9$ are each independently selected from substituted or unsubstituted $C_5$-$C_{40}$ aryl, substituted or unsubstituted $C_3$-$C_{40}$ heteroaryl; and a substituent is selected from any one or more of $C_1$-$C_{10}$ alkyl, $C_3$-$C_{10}$ cycloalkyl, $C_2$-$C_{10}$ alkenyl, $C_1$-$C_6$ alkoxyl, halogen, cyano, $C_6$-$C_{30}$ monocyclic aromatic hydrocarbon or fused ring aromatic hydrocarbon group, and $C_3$-$C_{30}$ monocyclic heteroaromatic hydrocarbon or fused ring heteroaromatic hydrocarbon group.

11. An organic electroluminescent device, comprising a first electrode and a second electrode, and an organic functional layer located between the first electrode and the second electrode, wherein the organic functional layer comprises a hole-blocking layer, and a transport material of the hole-blocking layer comprises the compound according to claim 1.

12. A display device, wherein the display device includes the organic electroluminescent device according to claim 11.

13. A compound, wherein the compound has a structure shown in Formula (I):

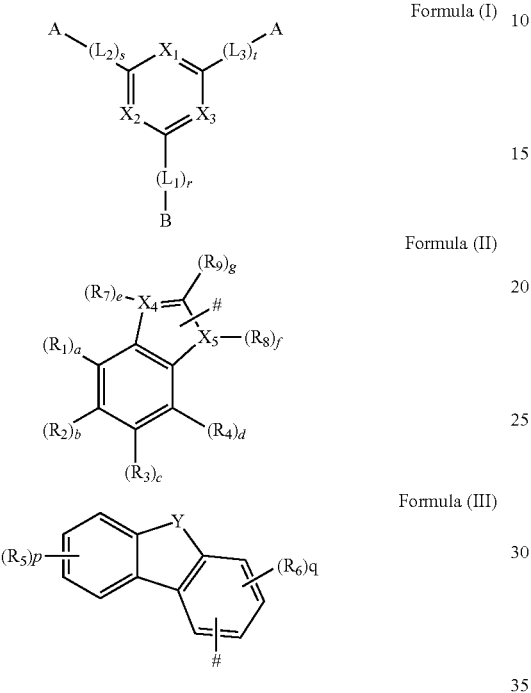

Formula (I)

Formula (II)

Formula (III)

wherein $X_1$-$X_3$ are all C—H groups; r, s, t are selected from 0, 1, wherein at least one of r, s, t is equal to 1, and $L_1$-$L_3$ are each independently selected from any one or more of the following groups:

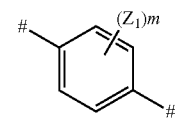

Chemical Formula 2-1

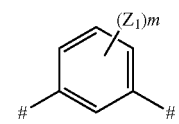

Chemical Formula 2-2

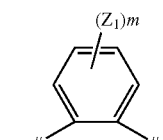

Chemical Formula 2-3

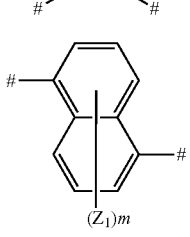

Chemical Formula 2-4

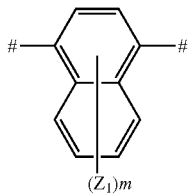

Chemical Formula 2-5

Chemical Formula 2-6

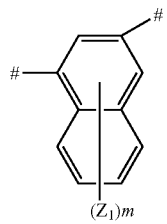

Chemical Formula 2-7

Chemical Formula 2-8

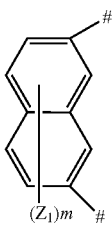

Chemical Formula 2-9

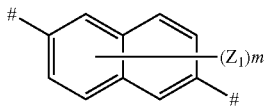

Chemical Formula 2-10

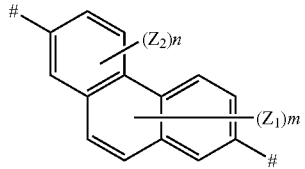

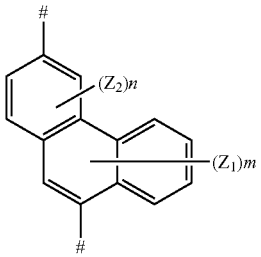

Chemical Formula 2-11

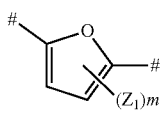

Chemical Formula 2-12

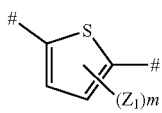

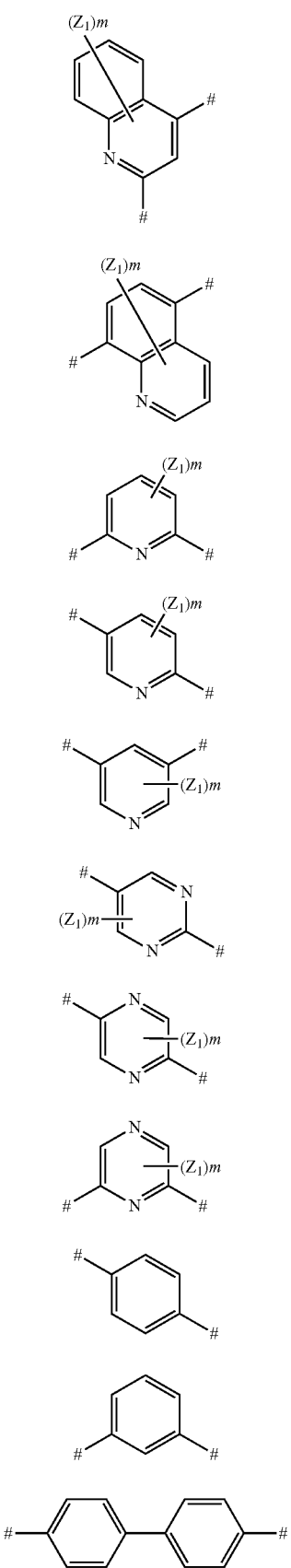
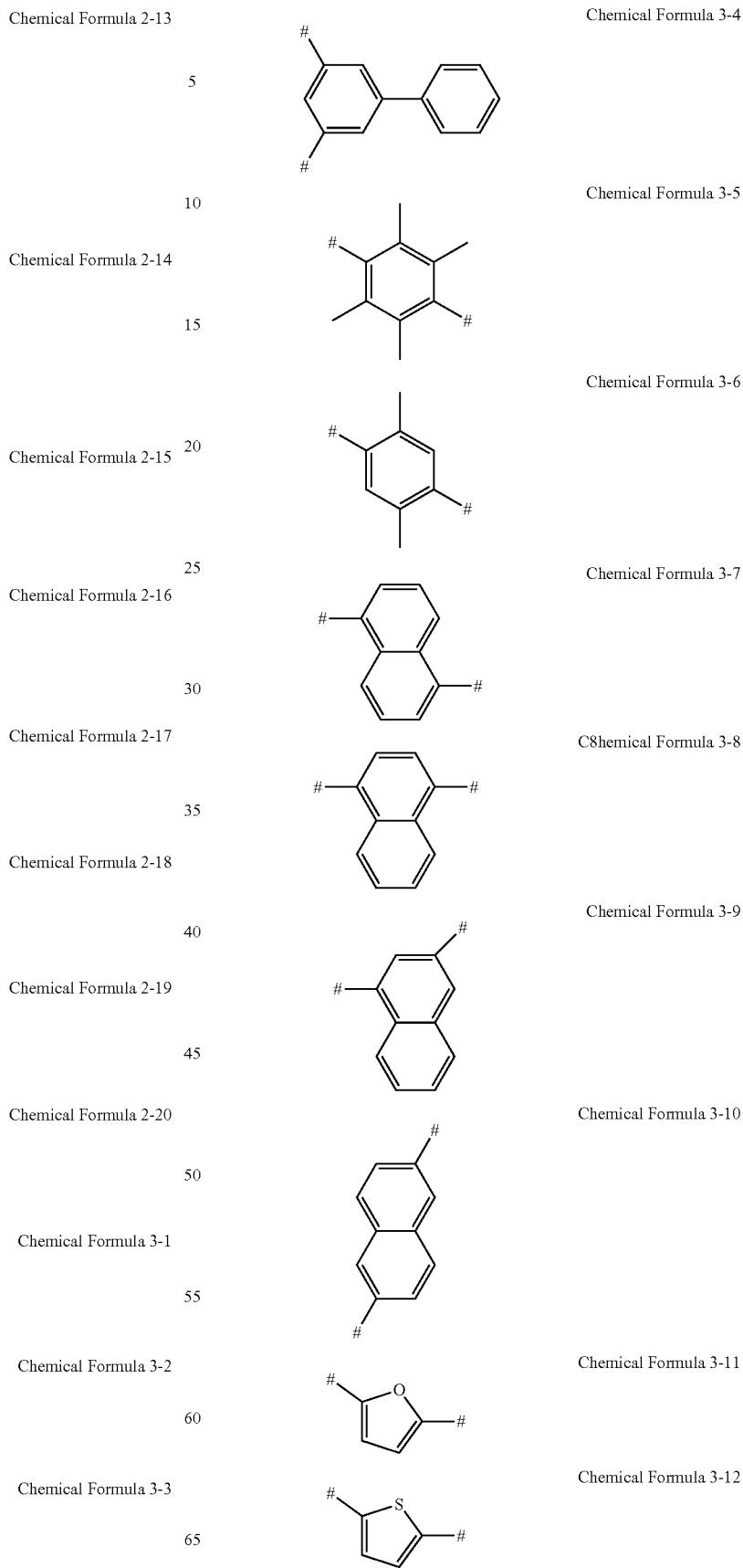

-continued

Chemical Formula 3-13
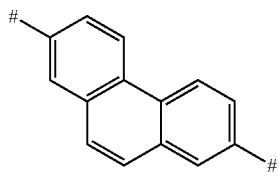

Chemical Formula 3-14
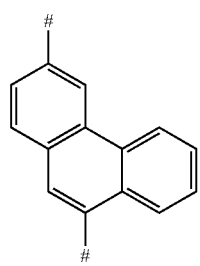

Chemical Formula 3-15
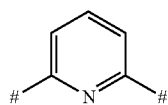

Chemical Formula 3-16
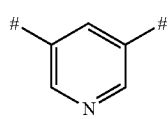

wherein $Z_1$ and $Z_2$ are each independently selected from any one or more of $C_1$-$C_{10}$ alkyl, $C_3$-$C_{10}$ cycloalkyl, $C_2$-$C_{10}$ alkenyl, $C_1$-$C_6$ alkoxyl, halogen, cyano, $C_6$-$C_{30}$ monocyclic heteroaromatic hydrocarbon or fused ring heteroaromatic hydrocarbon group, and $C_3$-$C_{30}$ monocyclic heteroaromatic hydrocarbon or fused ring heteroaromatic hydrocarbon group; m and n are each independently selected from 0, 1, or 2;

A is a structure shown in Formula (II), and B is a structure shown in Formula (III); in Formula (II), $X_4$ and $X_5$ are each independently selected from a C atom or an N atom, and at least one of them is an N atom; and a to f are each independently selected from 0, or 1, and g is 1;

in formula (III), Y is selected from an N atom, NPh, an O atom, or an S atom, when Y is an N atom, Formula (III) is joined to Formula (I) via the N atom;

$R_1$-$R_9$ are each independently selected from $C_1$-$C_{12}$ alkyl, substituted or unsubstituted $C_5$-$C_{40}$ aryl, and substituted or unsubstituted $C_3$-$C_{40}$ heteroaryl; and represents a connection location;

wherein one of p and q is 1, and one of p and q is 0, or p and q are each selected from 0.

14. The compound according to claim 13, wherein the compound is selected from any one of HB11
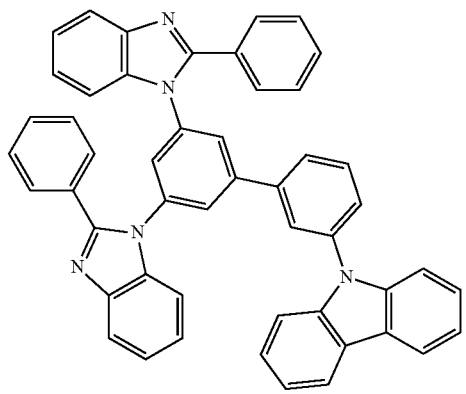

HB12
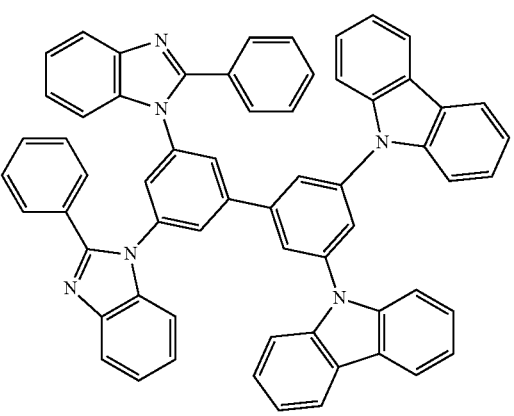

HB22
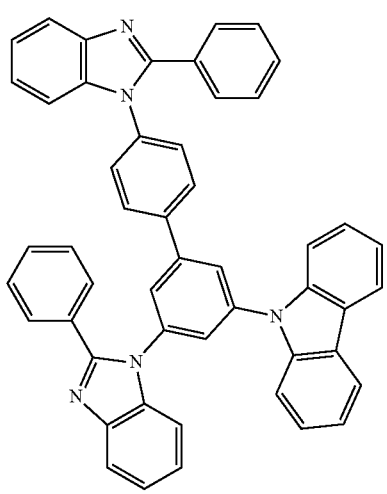

HB23 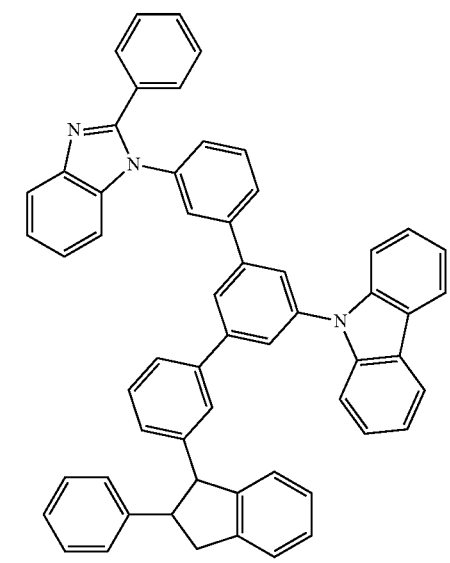
HB28 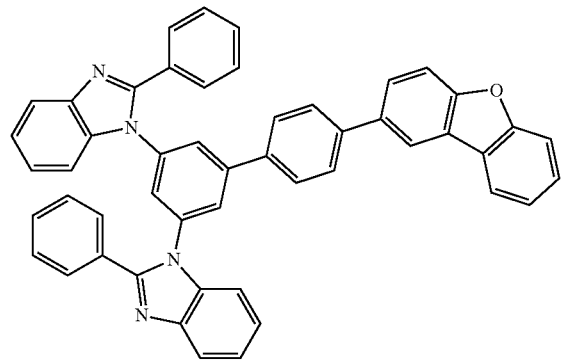
HB29 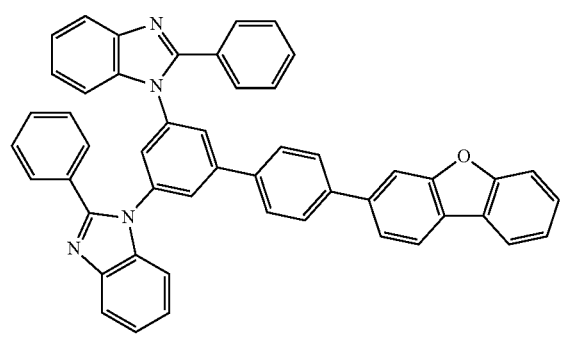
HB30 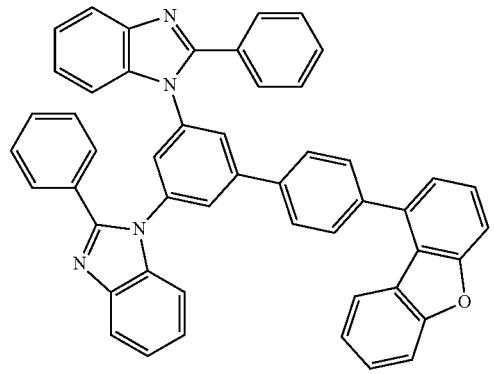
HB34 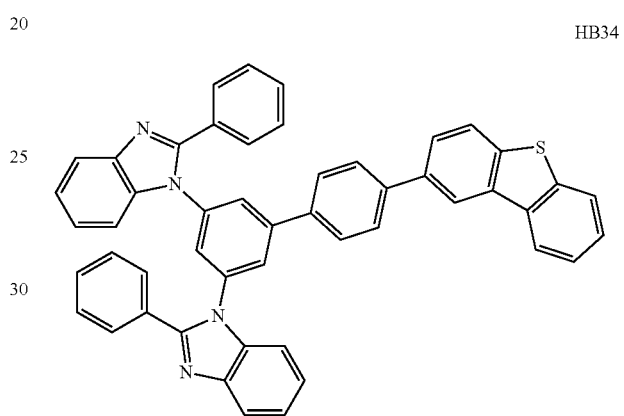
HB35 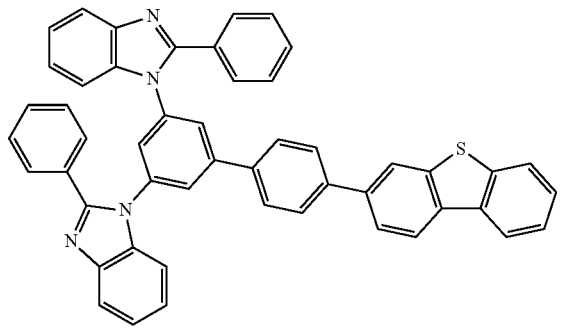
HB36 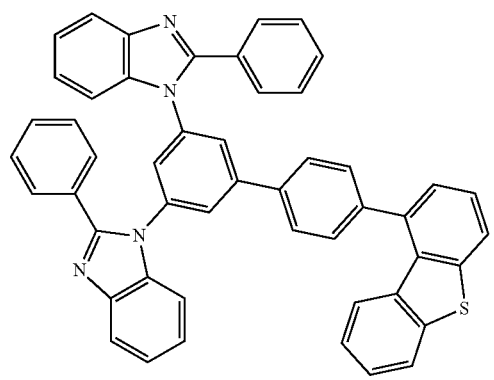

HB37 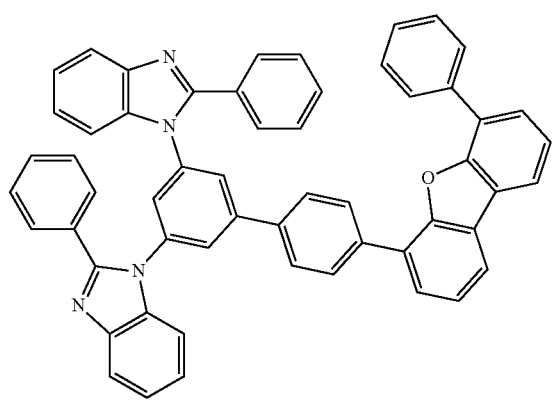
HB38 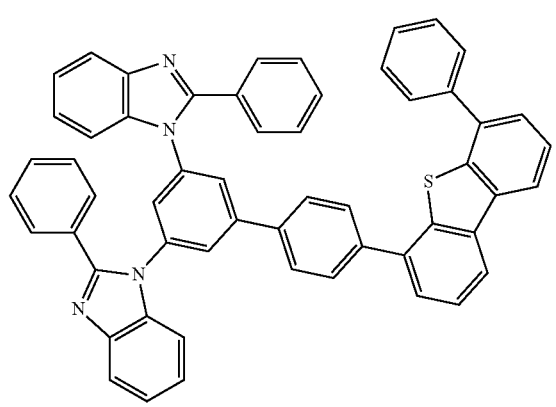
HB39 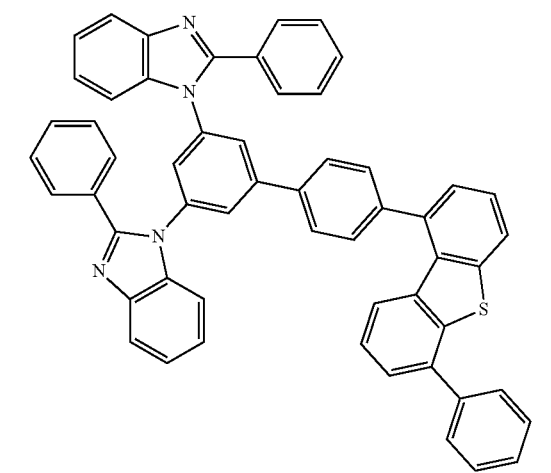
HB41 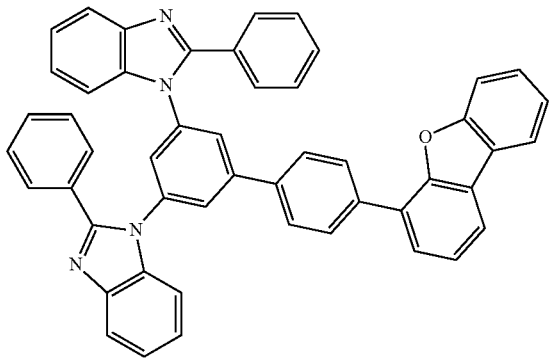
HB43 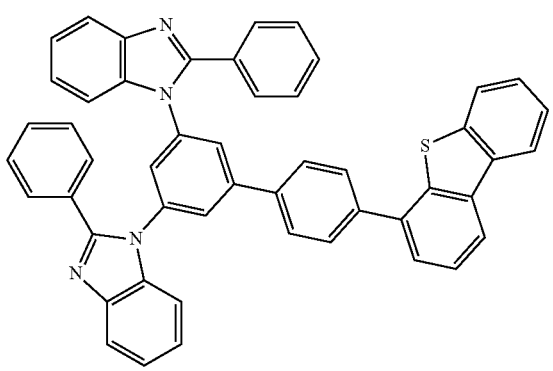
HB44 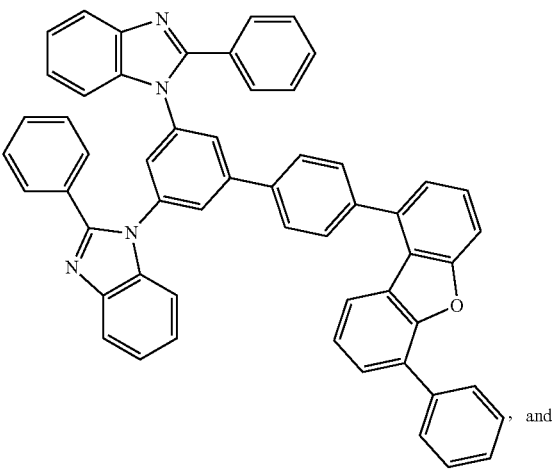
, and
HB47 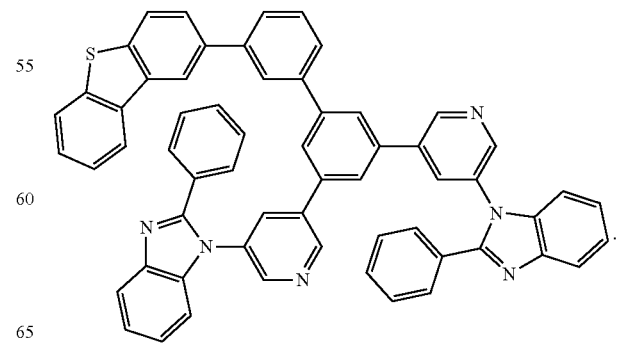

15. A compound, wherein the compound is selected from any one of:
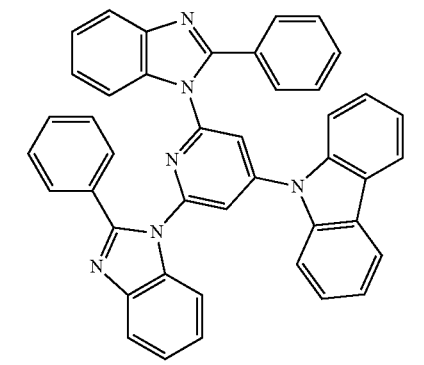
HB07
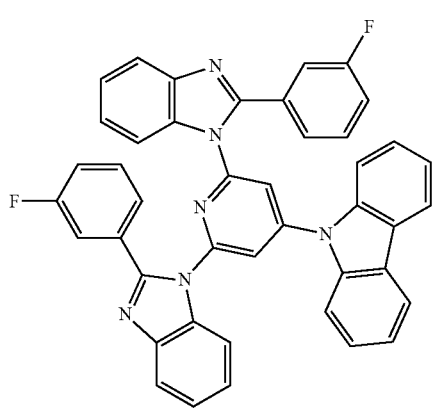
HB08
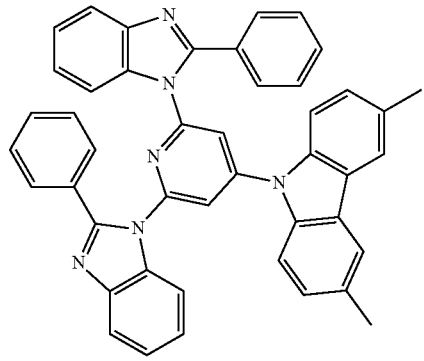
HB09
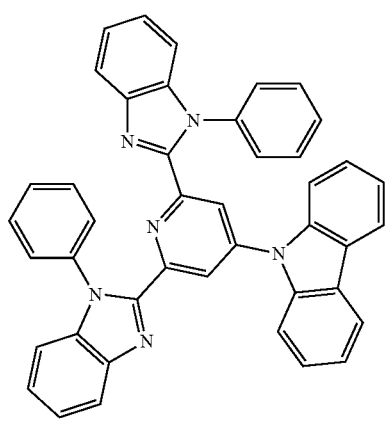
HB17
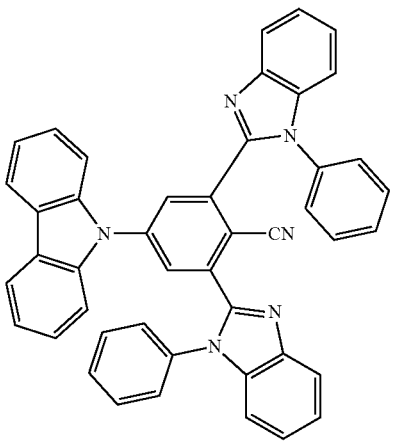
HB19
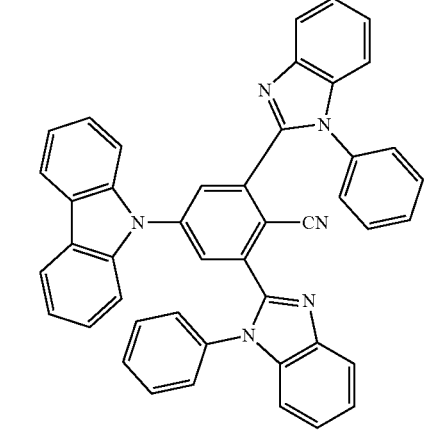
HB20
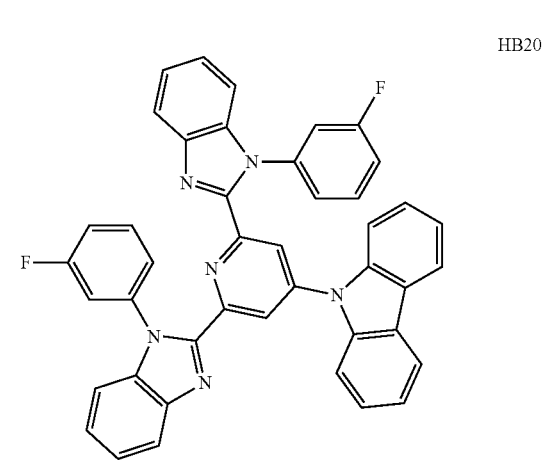
HB24
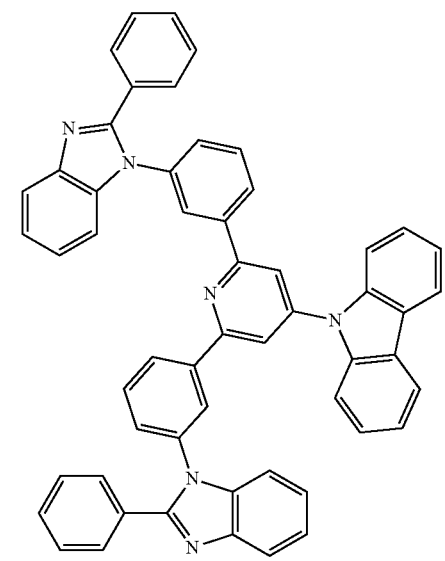

HB45
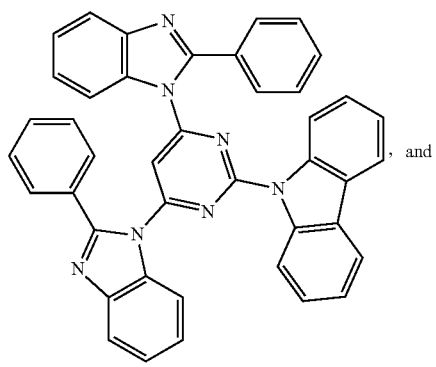
, and
HB46
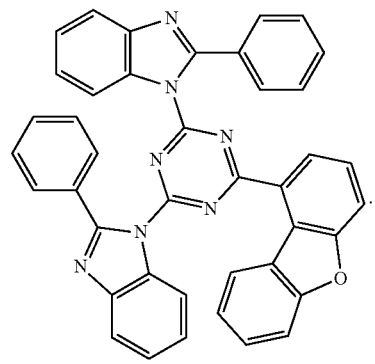
.
* * * * *